(12) United States Patent
Augeri et al.

(10) Patent No.: US 10,875,861 B1
(45) Date of Patent: Dec. 29, 2020

(54) THERAPEUTIC COMPOUNDS

(71) Applicant: Rutgers, The State University of New Jersey, New Brunswick, NJ (US)

(72) Inventors: David J. Augeri, New Brunswick, NJ (US); Hatem E. Sabaawy, New Brunswick, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/553,053

(22) Filed: Aug. 27, 2019

Related U.S. Application Data

(63) Continuation of application No. 15/990,464, filed on May 25, 2018, now abandoned.

(60) Provisional application No. 62/511,824, filed on May 26, 2017, provisional application No. 62/511,857, filed on May 26, 2017.

(51) Int. Cl.
| | | |
|---|---|---|
| *A61K 31/437* | (2006.01) | |
| *C07D 471/04* | (2006.01) | |
| *C07D 487/04* | (2006.01) | |
| *A61K 31/519* | (2006.01) | |
| *A61K 45/06* | (2006.01) | |
| *A61P 35/00* | (2006.01) | |

(52) U.S. Cl.
CPC .......... *C07D 471/04* (2013.01); *A61K 31/437* (2013.01); *A61K 31/519* (2013.01); *A61K 45/06* (2013.01); *A61P 35/00* (2018.01); *C07D 487/04* (2013.01)

(58) Field of Classification Search
CPC .............................. C07D 471/04; A61K 31/437
See application file for complete search history.

(56) References Cited

U.S. PATENT DOCUMENTS

| | | |
|---|---|---|
| 8,088,806 B2 | 1/2012 | Zhang et al. |
| 8,680,113 B2 | 3/2014 | Moon et al. |
| 2002/0041880 A1 | 4/2002 | Defeo-Jones et al. |
| 2012/0302573 A1 | 11/2012 | Jackson et al. |
| 2016/0046633 A1 | 2/2016 | Alimardanov et al. |

FOREIGN PATENT DOCUMENTS

| | | |
|---|---|---|
| EP | 2306836 B1 | 9/2016 |
| JP | 2003313176 A | 11/2003 |
| WO | 2010002985 A1 | 1/2010 |

OTHER PUBLICATIONS

Bartucci, M , et al., "Synthesis and Characterization of Novel BMI1 Inhibitors Targeting Cellular Self-Renewal in Hepatocellular Carcinoma", Target Oncol 12(4), 449-462 (2017).

Cao, L , et al., "BMI1 as a novel target for drug discovery in cancer", Journal of Cellular Biochemistry 112(10), 2729-2741 (2011).

Kim, M , et al., "Abstract 5517: PTC596induced Bmi1 hyperphosphorylation via Cdk1/2 activation resulting in tumor stem cell depletion", Proceedings: AACR Annual Meeting, San Diego, CA, Apr. 5-9, 2014.

Nishida, Y , et al., "The novel BMI-1 inhibitor PTC596 downregulates MCL-1 and induces p53-independent mitochondrial apoptosis in acute myeloid leukemia progenitor cells", Blood Cancer Journal 7, e527 (2017).

*Primary Examiner* — Brian E McDowell
(74) *Attorney, Agent, or Firm* — Viksnins Harris Padys Malen LLP

(57) ABSTRACT

The invention provides a compound of formula I:

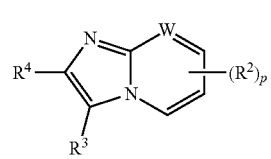

or a salt thereof, wherein $R^2$-$R^4$ and p have any of the values described in the specification, as well as compositions comprising a compound of formula I. The compounds are useful as anti-cancer agents.

3 Claims, 9 Drawing Sheets

THERAPEUTIC COMPOUNDS

CROSS-REFERENCE TO RELATED APPLICATIONS

This application is a continuation application of U.S. application Ser. No. 15/990,464, filed May 25, 2018, which claims the benefit of priority of Provisional Application No. 62/511,824, filed May 26, 2017 and Provisional Application No. 62/511,857, filed May 26, 2017, each of which is incorporated herein by reference in its entirety.

BACKGROUND

BMI-1 (B lymphoma Mo-MLV insertion region 1 homolog) protein is overexpressed in many tumors and is a critical component of polycomb repressive complex 1 (PRC1). Polycomb-repressive complex 1 (PRC1)-mediated histone ubiquitylation plays an important role in aberrant gene silencing in human cancers. Furthermore, this complex influences chromatin structure and regulates transcriptional activity of a number of important loci which encodes tumor suppressor proteins. Previous targeting of BMI-1 led to apoptosis and/or senescence in tumor cells in vitro and increases susceptibility to cytotoxic agents. Thus, BMI-1 is an attractive target in cancer therapy. Currently there is a need for agents that are useful for inhibiting BMI-1 expression.

SUMMARY

In one aspect the present invention provides compounds that are useful for inhibiting BMI-1 expression. Accordingly the invention provides a compound of formula I:

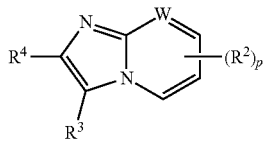

I wherein:

$R^3$ is $R^{3a}$ and $R^4$ is $R^{4a}$; or $R^3$ is $R^{3b}$ and $R^4$ is $R^{4b}$;

W is CH or N;

each $R^1$ is independently selected from the group consisting of hydroxy, halo, cyano, nitro, $C_{1-6}$ alkyl, $C_{1-6}$ alkoxy, $C_{1-6}$ alkanoyl, $C_{1-6}$ alkoxycarbonyl, $C_{2-6}$ alkanoyloxy, and —$N(R^a)_2$, wherein any $C_{1-6}$ alkyl or $C_{1-6}$ alkoxy is optionally substituted with one or more halo; or any two adjacent $R^1$ groups taken together form methylenedioxy or ethylenedioxy;

each $R^2$ is independently selected from the group consisting of hydroxy, halo, cyano, nitro, $C_{1-6}$ alkyl, $C_{1-6}$ alkoxy, $C_{1-6}$ alkanoyl, $C_{1-6}$ alkoxycarbonyl, $C_{2-6}$ alkanoyloxy, and —$N(R^a)_2$, wherein any $C_{1-6}$ alkyl or $C_{1-6}$ alkoxy is optionally substituted with one or more halo; or any two adjacent $R^1$ groups taken together form methylenedioxy or ethylenedioxy; $R^{3a}$ is:

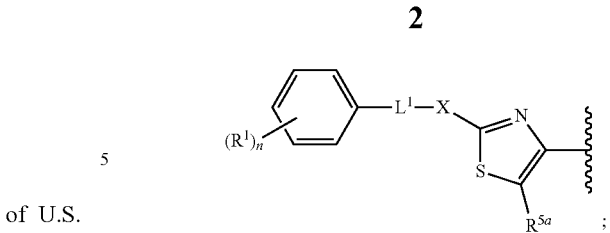

$R^{4a}$ is selected from the group consisting of hydrogen and $C_{1-6}$ alkyl that is optionally substituted with one or more halo;

$R^{3b}$ is selected from the group consisting of hydrogen and $C_{1-6}$ alkyl that is optionally substituted with one or more halo;

$R^{4b}$ is:

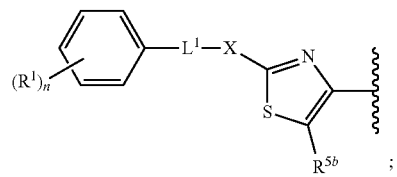

$L^1$ is absent or $C_{1-4}$ alkylene;

X is —$NR^x$—;

$R^{5a}$ is selected from the group consisting of hydrogen and $C_{1-6}$ alkyl that is optionally substituted with one or more halo;

$R^{5b}$ is selected from the group consisting of hydrogen and $C_{1-6}$ alkyl that is optionally substituted with one or more halo each $R^a$ is independently hydrogen or $C_{1-4}$ alkyl; or two $R^a$ groups taken together with the nitrogen to which they are attached form pyrrolidinyl, piperidinyl, piperazinyl or morpholinyl;

$R^x$ is hydrogen or $C_{1-4}$ alkyl;

n is 0, 1, 2, 3 or 4; and p is 0, 1, 2 or 3;

or a salt thereof.

The invention also provides a pharmaceutical composition comprising a compound of formula I or a pharmaceutically acceptable salt thereof, and a pharmaceutically acceptable excipient.

The invention also provides a method for treating or preventing cancer in an animal (e.g., a mammal such as a human) comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of cancer.

The invention also provides the use of a compound of formula I or a pharmaceutically acceptable salt thereof to prepare a medicament for treating cancer in an animal (e.g. a mammal such as a human).

The invention also provides processes and intermediates disclosed herein that are useful for preparing a compound of formula I or a salt thereof.

DETAILED DESCRIPTION

Figure 1:
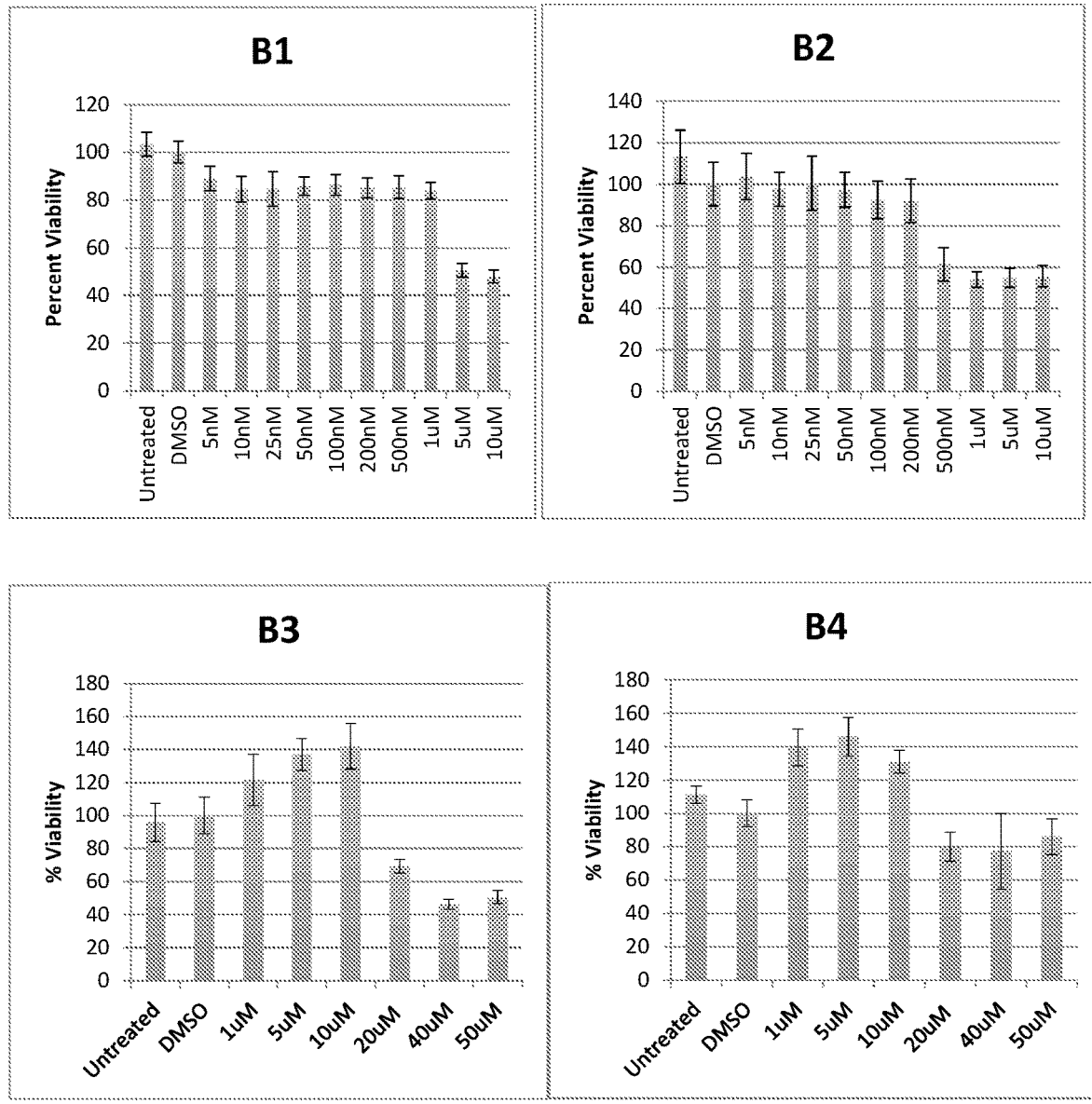
FIG. 1 shows in vitro EC50 data determined by MTT viability assay with glioblastoma cancer cell line for compounds B1, B2, B3 and B4.

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include ($C_1$-$C^8$)alkyl, ($C_2$—C)alkyl, $C_1$-$C_6$)alkyl, ($C_2$-$C_6$)alkyl and ($C_3$-$C_6$)alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkylene" by itself or as part of another substituent means a divalent radical derived from an alkane (including straight and branched alkanes), as exemplified by —$CH_2$—, —$CH_2CH_2CH_2CH_2$— and —$CH(CH_3)CH_2CH_2$—.

The term "alkoxy" refers to an alkyl groups attached to the remainder of the molecule via an oxygen atom ("oxy").

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

As used herein a wavy line "〜" that intersects a bond in a chemical structure indicates the point of attachment of the bond that the wavy bond intersects in the chemical structure to the remainder of a molecule.

The compounds disclosed herein can also exist as tautomeric isomers in certain cases. Although only one delocalized resonance structure may be depicted, all such forms are contemplated within the scope of the invention.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, (C$_1$-C$_6$)alkyl can be methyl, ethyl, propyl, isopropyl, butyl, iso-butyl, sec-butyl, pentyl, 3-pentyl, or hexyl; (C$_1$-C$_6$)alkoxy can be methoxy, ethoxy, propoxy, isopropoxy, butoxy, iso-butoxy, sec-butoxy, pentoxy, 3-pentoxy, or hexyloxy; (C$_1$-C$_6$)alkanoyl can be acetyl, propanoyl or butanoyl; (C$_1$-C$_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; and (C$_2$-C$_6$)alkanoyloxy can be acetoxy, propanoyloxy, butanoyloxy, isobutanoyloxy, pentanoyloxy, or hexanoyloxy.

In one embodiment the invention provides a compound of formula (I), which is a compound of formula (Ia):

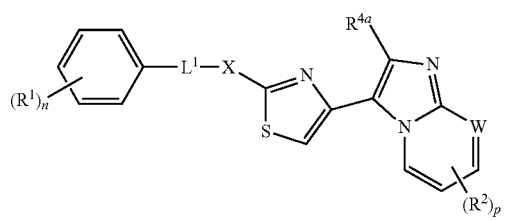

or a salt thereof.

In one embodiment the invention provides a compound of formula (I), which is a compound of formula (Ib):

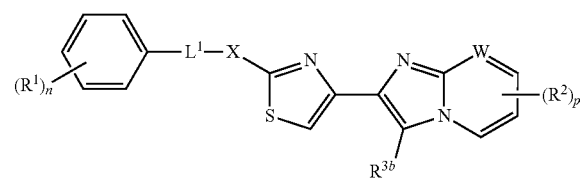

or a salt thereof.

In one embodiment the invention provides a compound of formula (I), which is a compound of formula (Ic):

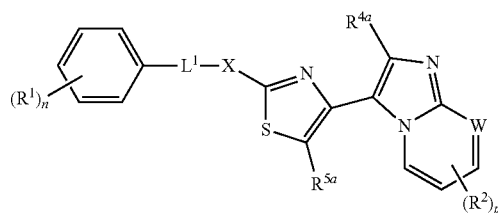

or a salt thereof.

In one embodiment the invention provides a compound of formula (I), which is a compound of formula (Id):

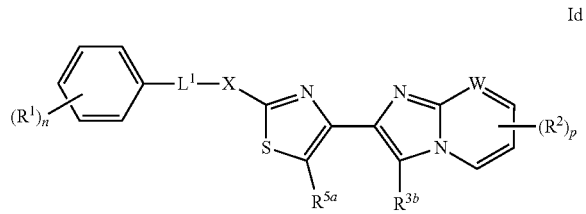

or a salt thereof.

In one embodiment, W is N.
In one embodiment, W is CH.
In one embodiment the invention provides a compound of formula (I), which is a compound of formula Ic:

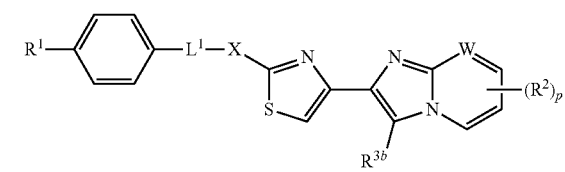

or a salt thereof.

In one embodiment, R$^1$ is C$_{1-6}$ alkoxy or —N(R$^a$)$_2$, wherein each R$^a$ is independently hydrogen or C$_{1-4}$ alkyl.
In one embodiment, R$^1$ is —OCH$_3$ or —N(CH$_3$)$_2$.
In one embodiment the invention provides a compound of formula (I), which is a compound of formula Id:

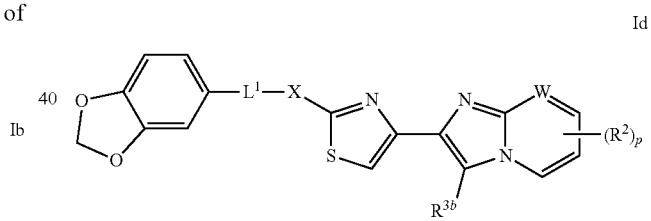

or a salt thereof.

In one embodiment, R$^{3b}$ is C$_{1-6}$ alkyl.
In one embodiment, R$^{3b}$ is —CH$_3$.
In one embodiment, X is —NH—.
In one embodiment, L is absent or —CH$_2$—.
In one embodiment, the compound of formula I is:

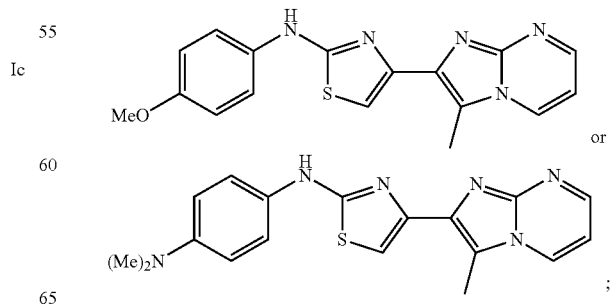

or a salt thereof.

In one embodiment, the compound of formula I is:

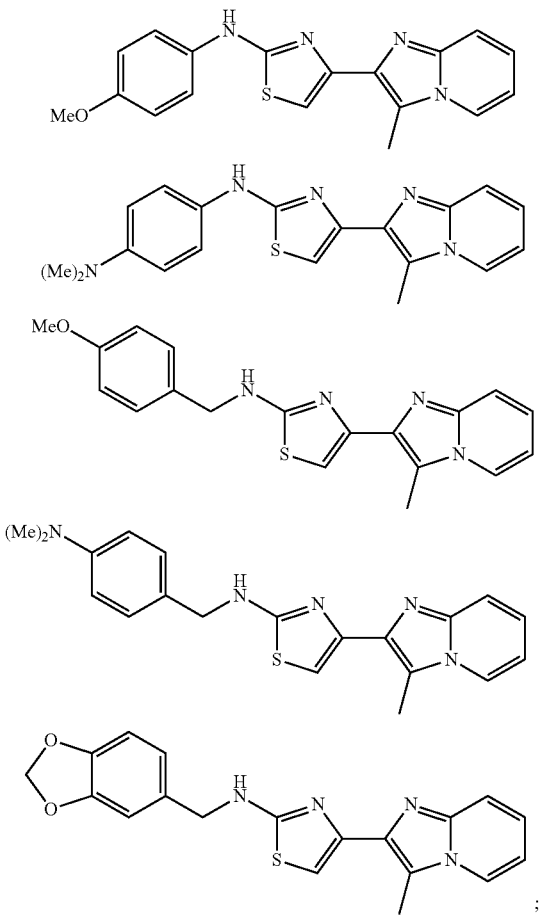

or a salt thereof.

In one embodiment, the compound of formula I is:

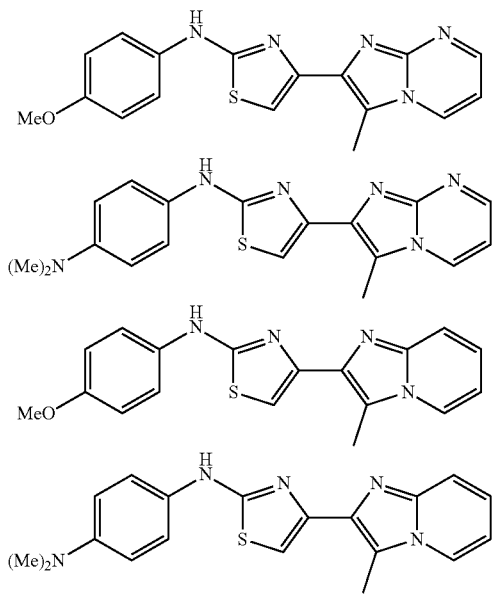

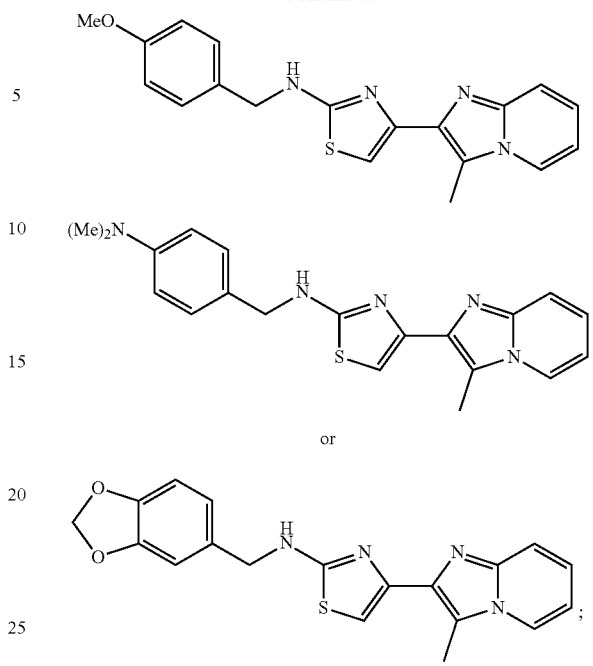

or a salt thereof.

In one embodiment the invention provides a compound of formula (I), which is a compound of formula Ie:

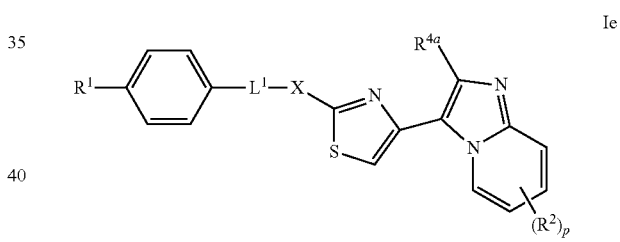

or a salt thereof.

In one embodiment the invention provides a compound of formula (I), which is a compound of formula If:

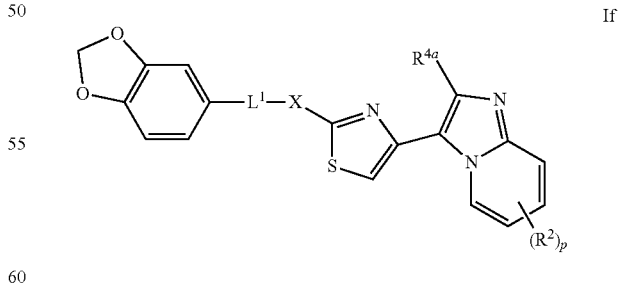

or a salt thereof.

In one embodiment, $R^{4a}$ is $C_{1-6}$ alkyl.
In one embodiment, $R^{4a}$ is —$CH_3$.
In one embodiment, X is —NH—.
In one embodiment, $L^1$ is absent.

In one embodiment, the compound of formula I is:

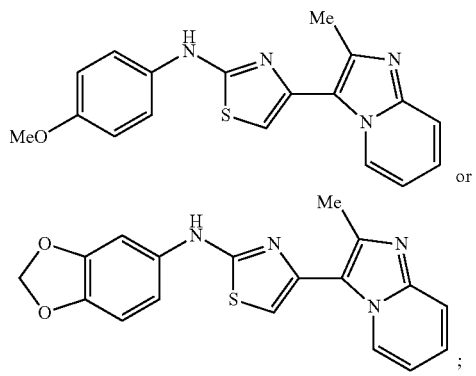

or a salt thereof.

In one embodiment, the cancer is selected from the group consisting of non-small cell lung cancer, breast cancer, prostate cancer, pancreatic cancer, head and neck cancer, medulloblastoma, glioblastoma, bile duct carcinoma, neuroblastoma, colon cancer, myeloma, gastric cancer, liver cancer, ovarian cancer, colorectal cancer, non-Hodgkin lymphoma, small-cell lung cancer, large cell lung cancer, kidney cancer, esophageal cancer, stomach cancer, cervical cancer, leukemia and lymphoma tumors.

In another aspect, the invention provides a method for inhibiting BMI-1 expression in an animal in need of comprising administering to the animal an effective amount of a compound of formula I or a pharmaceutically acceptable salt thereof.

In one embodiment, the method further comprises administering a compound of formula I, or a pharmaceutically acceptable salt thereof, in combination of one or more additional agents and optionally with radiation therapy.

In one embodiment, the one or more additional agents are selected from the groups consisting of anti-cancer agent, anti-proliferative agent, immunomodulatory agent, anti-angiogenic agent, anti-inflammatory agent, pain reliever, β2-agonist, anticholinergic agent, antihistamine, anti-malarial agent, anti-viral agent and antibiotic.

In another aspect, the invention provides a method for treating Huntington's disease in an animal comprising administering to the animal an effective amount of compound of formula I, or a pharmaceutically acceptable salt thereof.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for treating cancer. Examples of such agents include but not limited to cyclophosphamide, methotrexate, 5-fluorouracil, doxorubicin, and taxol. Accordingly, in one embodiment the invention also provides a composition comprising a compound of formula I, or a pharmaceutically acceptable salt thereof, at least one other therapeutic agent, and a pharmaceutically acceptable diluent or carrier. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal to treat cancer.

The ability of a compound of the invention to treat cancer may be determined using pharmacological models which are well known to the art, or using Tests A, B, and C described below.

Test A. Methylthiazolyldiphenyl-tetrazolium (MTT) assay

To generate primary patient-derived GBM models for testing small molecule inhibitors, fresh primary tissues were received from patients undergoing surgical resection of WHO grade IV gliomas at Robert Wood Johnson University Hospital (RWJUH) under an approved IRB protocol. De-identified primary human GBM samples were delivered to the laboratory. Cells were obtained through mechanical dissociation of the tumor tissue using a blade and plated in DMEM/F12 medium (Gibco) in the presence of B-27 Supplement (Gibco, #17504-044), 20 ng/ml of human recombinant EGF (Gibco, #PHG0311L) and human recombinant FGF (Peprotech, #AF-100-18B). The following day, the culture was collected, incubated with Accutase (Gibco, #A11105-01) at 37° C. and passed through a 26G×⅜ needle (BD Precision Glide, #305110) to obtain a single cell suspension and re-plated in the same supplemented medium. Cells were cultured at low (5-6) passages in serum-free sphere 3D culture with mitogens that preserve the clonogenic stemness phenotype. Four different primary GBM cells (GBM #46, GBM #50, and GBM #76) were tested for cell viability after treatment with the inhibitors. Cell viability was measured using MTT assay. Briefly, one thousand cells per well were seeded in 96-well plates and exposed to drug in a total of 200 uL media. After 72 hours, 50 uL of stock concentration of 2.5 mg/mL 3-(4,5-dimethylthiazol-2-yl)-2,5-diphenyltetrazolium bromide (MTT) (Sigma, #M2128) dissolved in PBS was added to wells and incubated at 37° C. for 4 hours; read in a fluorescent plate reader at 570 nm and compared to DMSO and untreated cells. The $IC_{50}$ (defined as the concentration at which 50% of the cells were viable) was determined from the curve.

Experimental results from Test A for representative compounds of the invention are shown in FIG. 1 and Table 1. These results demonstrate that compounds of the invention have anti-tumor activities. Accordingly, compounds of the invention may be useful as therapeutic agents for the treatment of cancer.

TABLE 1

In vitro EC50 data determined by MTT viability assay with glioblastoma cancer cell line

| Compound ID | EC50 (µM) |
|---|---|
| B1 | 5 |
| B2 | 1 |
| B3 | 20 |
| B4 | 20 (EC80) |

Test B. Modulation of BMI-1 and its downstream target ubiquitinated histone H2A

Different GBM cells were treated with DMSO or different concentrations of the B compounds for 72 hours. Cells were lysed in Cell Lysis Buffer (Cell Signaling, #9803) supplemented with Protease Inhibitor Cocktail (Sigma, #P8340), spun down for 30 minutes at 4° C., after which the supernatant was collected at every time point indicated. Western blotting analysis was performed on all samples as described above. BMI-1 loss started at 6-12 h, coinciding with an upper shift and hyper-phosphorylation of BMI-1 at 12-24 h and complete depletion at 72 h. The treatment with these inhibitors caused a dose-dependent reduction in BMI-1 and this was also associated with reduction in lysine-119 mono-ubiquitin form of yH2A, a specific product of BMI-1 (PRC1) activity.

Figure 2:
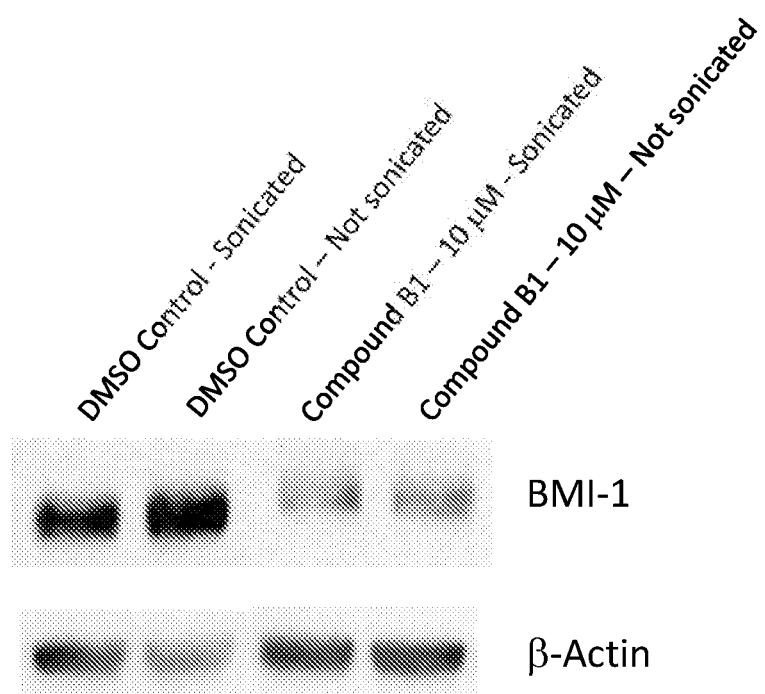
FIG. 2 shows modulation of BMI-1 by compound B1.
Figure 3:
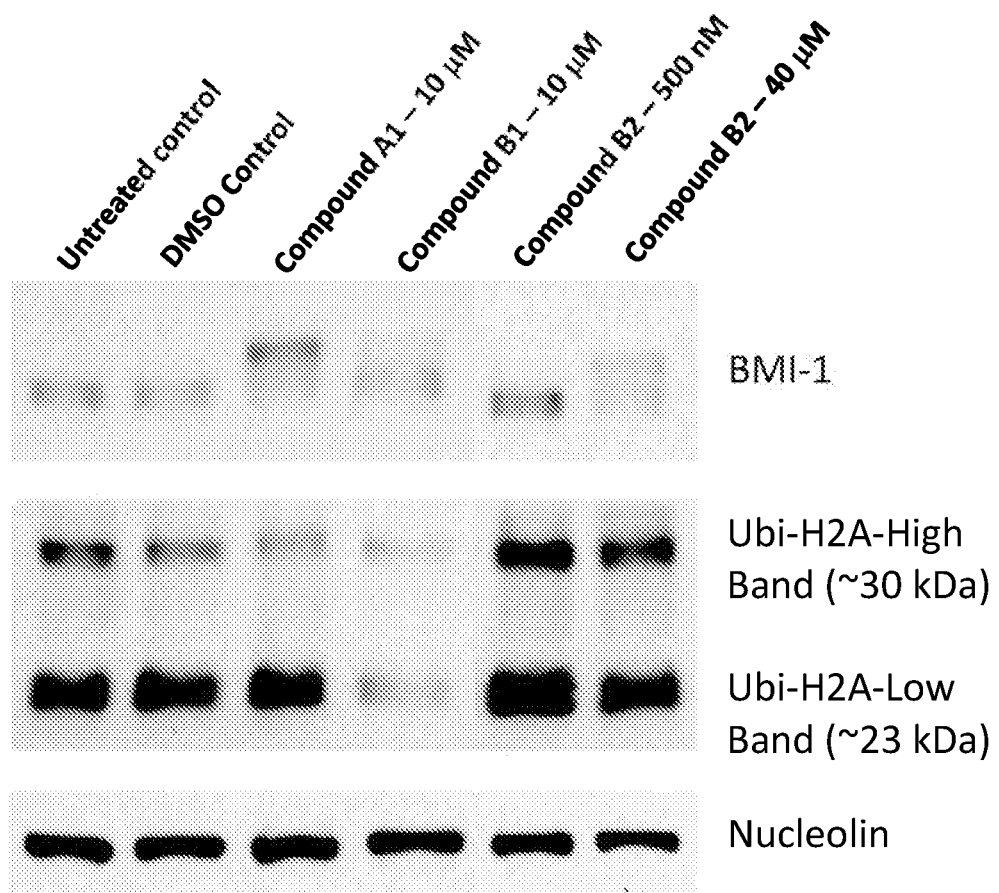
FIG. 3 shows modulation of downstream target ubiquitinated histone H2A by compounds B1 and B2.

Experimental results from Test B for representative compounds of the invention are shown in FIGS. 2 and 3. These results demonstrate that compounds of the invention inhibit Bmi-1 expression. BMI-1 protein is overexpressed in many tumors. Accordingly, compounds of the invention may be useful as therapeutic agents for the treatment of cancer.

Test C. Inhibition of BMI-1 protein in U87 cells by compound B1

U87 cells were treated with DMSO or different concentrations of compound B1 for 72 hours. Cells were lysed in Cell Lysis Buffer (Cell Signaling, #9803) supplemented with Protease Inhibitor Cocktail (Sigma, #P8340), sonicated briefly while on ice and spun down for 30 minutes at 4° C., after which the supernatant was collected. For each sample, 2 uL of lysate was mixed well into 198 uL de-ionized water. Next, 10 uL of this diluted sample was added to a well in a 96 well plate in quadruplets and mixed with Protein Assay Dye Reagent Concentrate (Bio-Rad, #500-0006) (which was diluted 1:5 with water). BSA standards of 25 ng, 50 ng, 100 ng, 200 ng and 250 ng were also used to the plate and mixed with the reagent. The plate was read in a plate reader at 600 nm and samples were calibrated to the standards to determine the concentration of protein. Using the NuPAGE system (Invitrogen), 25 ug of protein was mixed with NuPAGE LDS 4× Sample Buffer (#NP0007), NuPAGE 10× Reducing Agent (#NP0004) and water, mixed well and heated at 96° C. for 15 minutes to denature the protein. The samples were then loaded into 4-12% Bis-Tris gels (Novex (Invitrogen), #0323) with a protein ladder (Novex (Invitrogen) Sharp Pre-stained protein ladder, #57318) and run at 100-120V for about 2 hours with NuPAGE 20×SDS MES Running Buffer (#NP0002) diluted with water. Next, the gel was taken out and loaded into a NuPAGE transfer cassette with a polyvinylidene membrane with NuPAGE 20× Transfer Buffer (#NP0006-1) diluted with water and methanol. Proteins were transferred for 1 hour at 30V at room temperature. Blocking was performed using the Millipore SNAP i.d. Protein Detection system in 0.25% non-fat dry milk in 0.1% Tween in PBS (PBST). Primary antibodies against BMI-1 (Cell Signaling, #6964) and housekeeping control rabbit polyclonal anti-vinculin (1:1000) (Cell Signaling) were incubated overnight with gentle rocking at 4° C. in the blocking solution. The following day, membranes were washed 3 times with PBST in the SNAP i.d. system before being incubated with secondary antibody in blocking buffer for 1 hour at room temperature. Three washes were then performed in the SNAP i.d. system. Protein signals were detected using ECL Western Blotting Substrate (Pierce, #32106) and filmed.

Figure 4:
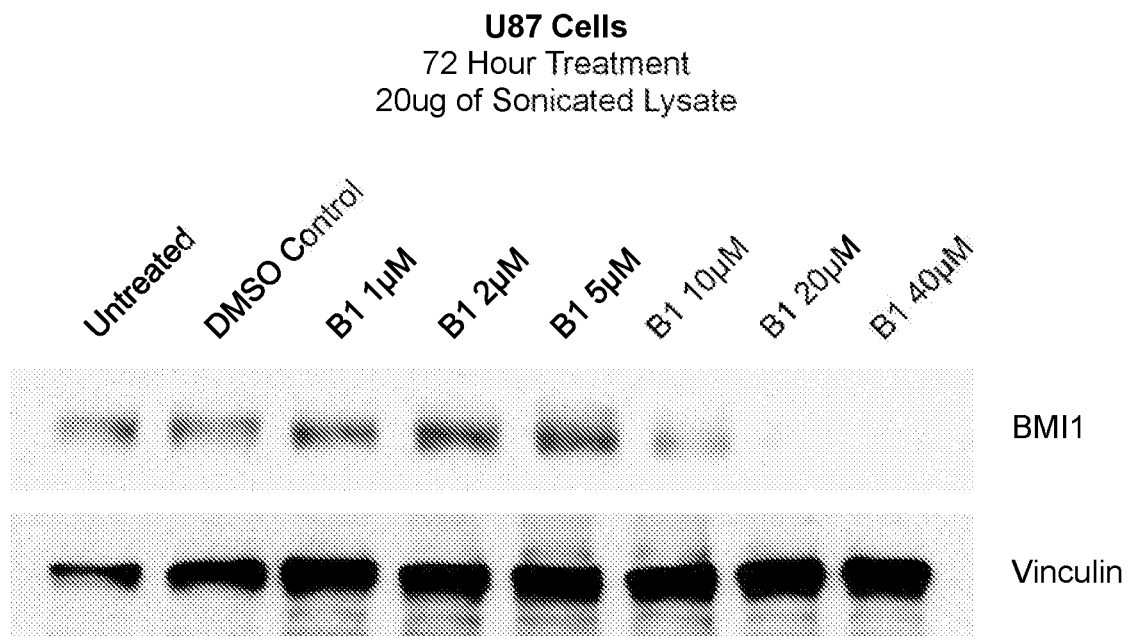
FIG. 4 shows inhibition of BMI-1 protein levels by compound B1 in U87 cells. Western blotting was performed on 20 micrograms of sonicated U87 glioblastoma cell lysate treated for 72 hours at different concentrations for compound B1.

Experimental results from Test C for representative compound of the invention are shown in FIG. 4. These results demonstrate that compounds of the invention inhibit BMI-1 expression. BMI-1 protein is overexpressed in many tumors. Accordingly, compounds of the invention may be useful as therapeutic agents for the treatment of cancer.

Compounds of invention can be prepared using known methods or using procedures analogous to those described in the examples herein.

The invention will now be illustrated by the following non-limiting Examples.

EXAMPLES

Example 1. Synthesis of Representative Compounds B1-B4

Step 1. Synthesis of 1-(imidazo[1,2-a]pyridin-2-yl)ethan-1-one (4)

To biacetyl (1) (6.72 ml, 76.6 mmol, 2.4 eq) stirring at 0° C. was added $Br_2$ (2.63 ml, 51.0 mmol, 1.6 eq) dropwise. The reaction was allowed to warm to rt and stirred for 1 hour to give a crude solution of 1-bromobutane-2,3-dione (2) which was used without purification. A solution of pyridin-2-amine (3) (3.0 g, 31.9 mmol, 1.0 eq) in EtOH (65 ml) was added slow at rt, followed by heating for 16 hours at 80° C. The reaction was partitioned in $DCM/H_2O$ followed by addition of a sufficient volume of $Na_2S_2O_3$ (sat, aq) to quench any remaining $Br_2$. The aqueous was adjusted to pH=8 with $NaHCO_3$ (sat, aq) and extracted 3×DCM, dried over $Na_2SO_4$, filtered and concentrated. The crude residue was purified by silica gel chromatography, eluting in (2% MeOH/DCM→5% MeOH/DCM) followed by repurification of product containing fractions by silica gel chromatography (25% EtOAc/Hex→50% EtOAc/Hex). Product fractions were concentrated, recrystallized from EtOAc, filtered and dried under vacuum to afford 1-(imidazo[1,2-a]pyridin-2-yl)ethan-1-one (4) (509 mg, 3.18 mmol, 10% yield, 95% purity) as a white solid. $^1$H NMR (500 MHz, Chloroform-d) δ 8.17-8.11 (m, 2H), 7.67 (dq, J=9.2, 1.0 Hz, 1H), 7.27-7.24 (m, 1H), 6.87 (td, J=6.8, 1.1 Hz, 1H), 2.72 (s, 3H). MS m/z: 160.85 [M+1]⁺.

Step 2. Synthesis of 1-(3-bromoimidazo[1,2-a]pyridin-2-yl)ethan-1-one (5)

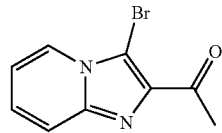

To a solution of 1-(imidazo[1,2-a]pyridin-2-yl)ethan-1-one (4) (373 mg, 2.33 mmol, 1 eq) in MeCN (20 ml) was added NBS (415 mg, 2.33 mmol, 1 eq). After stirring for 2 hours at rt, the reaction was quenched with $Na_2S_2O_3$ (sat, aq), and concentrated to remove majority of MeCN. The crude reaction was partitioned in $DCM/H_2O$ and extracted 3×DCM, dried over $Na_2SO_4$, filtered and concentrated. Purification by silica gel chromatography (25% EtOAc/Hex) followed by concentration afforded 1-(3-bromoimidazo[1,2-a]pyridin-2-yl)ethan-1-one (5) (447 mg, 1.87 mmol, 80% yield, 90% purity) as a white solid. ¹H NMR (500 MHz, Chloroform-d) δ 8.20 (dq, J=7.0, 1.3 Hz, 1H), 7.65 (dq, J=9.2, 1.2 Hz, 1H), 7.33 (ddt, J=9.3, 6.7, 1.3 Hz, 1H), 7.00 (tt, J=6.9, 1.2 Hz, 1H), 2.79-2.71 (m, 3H). MS m/z: 240.7 [M+1]⁺.

Step 3. Synthesis of 1-(3-methylimidazo[1,2-a]pyridin-2-yl)ethan-1-one (6)

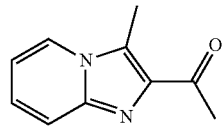

A mixture of 1-(3-bromoimidazo[1,2-a]pyridin-2-yl)ethan-1-one (5) (445 mg, 1.86 mmol, 1 eq), methylboronic acid (446 mg, 7.46 mmol, 4 eq), $PdC_2(PPh_3)_2$ (65 mg, 0.0932 mmol, 0.05 eq), dioxane (9 ml) and 2M $Na_2CO_3$ (aq, 9 ml) was added to a microwave vial and heated 10 min at 140° C. The crude reaction was partitioned in $EtOAc/H_2O$ and filtered over celite to remove undissolved palladium. The aqueous was extracted 2×EtOAc, and concentrated. The residue was partitioned in iN HCl (aq)/EtOAc and extracted 2×1 N HCl (aq). The aqueous was made basic with NaOH, extracted 3×EtOAc, dried over $Na_2SO_4$, filtered and concentrated. Purification by silica gel chromatography (25% EtOAc/Hex→50% EtOAc/Hex) afforded 1-(3-methylimidazo[1,2-a]pyridin-2-yl)ethan-1-one (6) (175 mg, 1.0 mmol, 54% yield, 98% purity) as a white solid and HBr salt.

¹H NMR (500 MHz, DMSO-d₆) δ 8.34 (dt, J=7.0, 1.2 Hz, 1H), 7.62 (dt, J=9.2, 1.1 Hz, 1H), 7.32 (ddd, J=9.2, 6.7, 1.2 Hz, 1H), 7.01 (td, J=6.8, 1.2 Hz, 1H), 2.71 (s, 3H), 2.57 (s, 3H). MS m/z: 174.9 [M+1]⁺.

Step 4. Synthesis of 2-bromo-1-(3-methylimidazo[1,2-a]pyridin-2-yl)ethan-1-one (11)

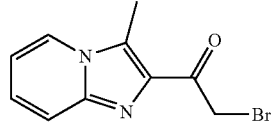

To a mixture of 1-(3-methylimidazo[1,2-a]pyridin-2-yl)ethan-1-one (6) (173 mg, 0.99 mmol, 1 eq) in AcOH (13 ml) was added 33% HBr/AcOH (300 uL) followed by Br₂ (42.8 uL, 0.832 mmol, 1.05 eq). The reaction was stirred 3 hours at rt, followed by dilution in DCM (200 ml) to precipitate a solid that was filtered. This filtered solid was triturated in MeOH, sonicated and filtered to give 2-bromo-1-(3-methylimidazo[1,2-a]pyridin-2-yl)ethan-1-one (11) (280 mg, 0.84 mmol, 84% yield, 98% purity) as a white solid. ¹H NMR (500 MHz, DMSO-d₆) δ 8.52 (dt, J=7.2, 1.1 Hz, 1H), 7.72 (dt, J=9.2, 1.0 Hz, 1H), 7.55 (ddd, J=9.1, 6.9, 1.2 Hz, 1H), 7.19 (td, J=6.8, 1.1 Hz, 1H), 4.88 (s, 2H), 2.77 (s, 3H). MS m/z: 252.8, 254.85 [M+1]⁺.

Step 5. Synthesis of 2-bromo-1-(3-methylimidazo[1,2-a]pyrimidin-2-yl)ethan-1-one (10)

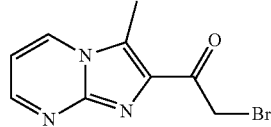

1-(3-methylimidazo[1,2-a]pyrimidin-2-yl)ethan-1-one (9) (100 mg, 0.571 mmol, 1 eq) was taken up in AcOH (1 ml). To this mixture was added 33% HBr/AcOH (214 uL) followed by Br₂ (30.8 uL). The reaction was stirred 16 hours at rt, followed by partitioning in NaHCO₃ (sat, aq) and DCM. The aqueous was extracted 2×DCM and the combined organic was washed 1×brine, dried over Na₂SO₄, filtered and concentrated. The crude was purified by silica gel chromatography (100% EtOAc), and the product containing fractions were concentrated to afford 2-bromo-1-(3-methylimidazo[1,2-a]pyrimidin-2-yl)ethan-1-one (10) (80 mg, 0.32 mmol, 55% yield) as a light pink solid. MS m/z: 252.8, 254.85 [M+1]⁺.

Step 6. Synthesis of Compounds B1-B4

N-(4-methoxyphenyl)-4-(3-methylimidazo[1,2-a]pyridin-2-yl)thiazol-2-amine(B3)

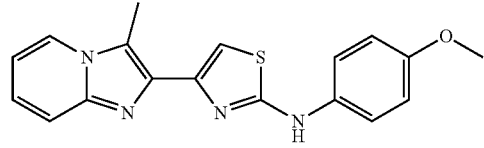 [SMILES: COc1ccc(Nc2nc(-c3nc4ccccn4c3C)cs2)cc1]

2-bromo-1-(3-methylimidazo[1,2-a]pyridin-2-yl)ethan-1-one (11) (50 mg, 0.15 mmol, 1 eq) and 1-(4-methoxyphenyl)

thiourea (12) (27 mg, 0.15 mmol, 1 eq) were taken up in MeCN (3 ml) and MeOH (3 ml) and heated 3 hours at 70° C. The crude reaction was concentrated, partitioned in a mixture of (5% MeOH/DCM)/H$_2$O, extracted 4×5% MeOH/DCM, dried over Na$_2$SO$_4$, filtered and concentrated. The crude product was purified by silica gel chromatography (50% EtOAc/Hex→100% EtOAc/Hex). After concentrating the product containing fractions, the residue was recrystallized from a mixture of DCM/Hexanes, sonicated, filtered and dried under vacuum to afford N-(4-methoxyphenyl)-4-(3-methylimidazo[1,2-a]pyridin-2-yl)thiazol-2-amine (B3) (33.2 mg, 0.99 mmol, 66% yield, >98% purity) as a light yellow solid. $^1$H NMR (500 MHz, DMSO-d$_6$) δ 10.01 (s, 1H), 8.26 (dt, J=6.9, 1.1 Hz, 1H), 7.64-7.57 (m, 2H), 7.50 (dt, J=9.1, 1.1 Hz, 1H), 7.22 (ddd, J=9.0, 6.7, 1.2 Hz, 1H), 7.16 (s, 1H), 6.95-6.88 (m, 3H), 3.72 (s, 3H), 2.86 (s, 3H). MS m/z: 337.05 [M+1]$^+$.

N-(4-methoxyphenyl)-4-(3-methylimidazo[1,2-a]pyrimidin-2-yl)thiazol-2-amine(B1)

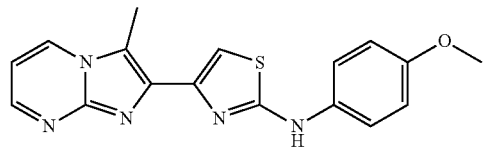 [SMILES: COc1ccc(Nc2nc(-c3nc4ncccn4c3C)cs2)cc1]

Following the procedure as described in the synthesis of (B3), reaction of 2-bromo-1-(3-methylimidazo[1,2-a]pyrimidin-2-yl)ethan-1-one (10) (and 1-(4-methoxyphenyl) thiourea (12) afforded N-(4-methoxyphenyl)-4-(3-methylimidazo[1,2-a]pyrimidin-2-yl)thiazol-2-amine (B1) (34.4 mg, 0.102 mmol, 32% yield, >95% purity) as a yellow solid after recrystallization from MeOH. MS m/z: 338.05 [M+1]$^+$.

N$^1$,N$^1$-dimethyl-N$^4$-(4-(3-methylimidazo[1,2-a]pyrimidin-2-yl)thiazol-2-yl)benzene-1,4-diamine (B2)

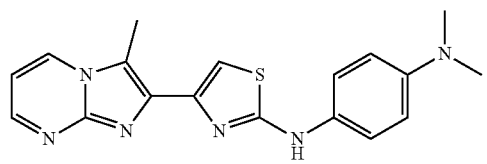 [SMILES: Cc1c(-c2csc(Nc3ccc(N(C)C)cc3)n2)nc2ncccn12]

Following the procedure as described in the synthesis of (B3), reaction of 2-bromo-1-(3-methylimidazo[1,2-a]pyrimidin-2-yl)ethan-1-one (10) (171 mg, 0.67 mmol) and 1-(4-(dimethylamino)phenyl)-thiourea (13) (132 mg, 0.67 mmol, 1 eq)) afforded N$^1$,N$^1$-dimethyl-N$^4$-(4-(3-methylimidazo[1,2-a]pyrimidin-2-yl)thiazol-2-yl)benzene-1,4-diamine (B2) in 2 crops of crystals, 61 mg and 8 mg for a total of 69 mg of B2. The 8 mg crop was >95% purity as a yellow solid after recrystallization from MeOH. MS m/z: 350.44 [M+1]$^+$.

N$^1$,N$^1$-dimethyl-N$^4$-(4-(3-methylimidazo[1,2-a]pyridin-2-yl)thiazol-2-yl)benzene-1,4-diamine (B4)

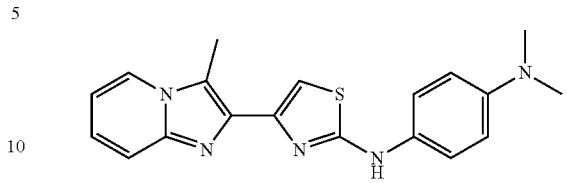

Following the procedure as described in the synthesis of (B3), reaction of 2-bromo-1-(3-methylimidazo[1,2-a]pyridin-2-yl)ethan-1-one (11) (50 mg, 0.15 mmol, 1 eq) and 1-(4-(dimethylamino)phenyl)thiourea (13) (29 mg, 0.15 mmol, 1 eq) afforded N$^1$,N$^1$-dimethyl-N$^4$-(4-(3-methylimidazo[1,2-a]pyridin-2-yl)thiazol-2-yl)benzene-1,4-diamine (B4) (31.7 mg, 0.091 mmol, 60% yield, >99% purity) as a yellow/green solid after recrystallization from EtOAc. $^1$H NMR (500 MHz, DMSO-d$_6$) δ 9.81 (s, 1H), 8.24 (dt, J=7.0, 1.2 Hz, 1H), 7.53-7.46 (m, 3H), 7.22 (ddd, J=9.1, 6.7, 1.2 Hz, 1H), 7.10 (s, 1H), 6.91 (td, J=6.8, 1.2 Hz, 1H), 6.78-6.71 (m, 2H), 2.86 (s, 3H), 2.84 (s, 6H). MS m/z: 349.80 [M+1]$^+$.

Example 2. Biological Assays

MTT assay

To generate primary patient-derived GBM models for testing small molecule inhibitors, fresh primary tissues were received from patients undergoing surgical resection of WHO grade IV gliomas at Robert Wood Johnson University Hospital (RWJUH) under an approved RB protocol. De-identified primary human GBM samples were delivered to the laboratory. Cells were obtained through mechanical dissociation of the tumor tissue using a blade and plated in DMEM/F12 medium (Gibco) in the presence of B-27 Supplement (Gibco, #17504-044), 20 ng/ml of human recombinant EGF (Gibco, #PHG0311L) and human recombinant FGF (Peprotech, #AF-100-18B). The following day, the culture was collected, incubated with Accutase (Gibco, #A11105-01) at 37° C. and passed through a 26G× ⅜ needle (BD Precision Glide, #305110) to obtain a single cell suspension and re-plated in the same supplemented medium. Cells were cultured at low (5-6) passages in serum-free sphere 3D culture with mitogens that preserve the clonogenic sternness phenotype. Four different primary GBM cells (GBM #46, GBM #50, and GBM #76) were tested for cell viability after treatment with the inhibitors. Cell viability was measured using MTT assay. Briefly, one thousand cells per well were seeded in 96-well plates and exposed to drug in a total of 200 uL media. After 72 hours, 50 uL of stock concentration of 2.5 mg/mL 3-(4,5-dimethylthiazol-2-yl)-2,5-diphenyltetrazolium bromide (MTT) (Sigma, #M2128) dissolved in PBS was added to wells and incubated at 37° C. for 4 hours; read in a fluorescent plate reader at 570 nm and compared to DMSO and untreated cells. The IC$_{50}$ (defined as the concentration at which 50% of the cells were viable) was determined from the curve.

Modulation of BMI-1 and its Downstream Target Ubiquitinated Histone H2A

Different GBM cells were treated with DMSO or different concentrations of the B compounds for 72 hours. Cells were lysed in Cell Lysis Buffer (Cell Signaling, #9803) supplemented with Protease Inhibitor Cocktail (Sigma, #P8340), spun down for 30 minutes at 4° C., after which the supernatant was collected at every time point indicated. Western blotting analysis was performed on all samples as described above. BMI-1 loss started at 6-12 h, coinciding with an upper shift and hyper-phosphorylation of BMI-1 at 12-24 h and complete depletion at 72 h. The treatment with these inhibitors caused a dose-dependent reduction in BMI-1 and this was also associated with reduction in lysine-119 mono-ubiquitin form of yH2A, a specific product of BMI-1 (PRC1) activity.

Inhibition of BMI-1 Protein in U87 Cells by Compound B1

U87 cells were treated with DMSO or different concentrations of compound B1 for 72 hours. Cells were lysed in Cell Lysis Buffer (Cell Signaling, #9803) supplemented with Protease Inhibitor Cocktail (Sigma, #P8340), sonicated briefly while on ice and spun down for 30 minutes at 4° C., after which the supernatant was collected. For each sample, 2 uL of lysate was mixed well into 198 uL de-ionized water. Next, 10 uL of this diluted sample was added to a well in a 96 well plate in quadruplets and mixed with Protein Assay Dye Reagent Concentrate (Bio-Rad, #500-0006) (which was diluted 1:5 with water). BSA standards of 25 ng, 50 ng, 100 ng, 200 ng and 250 ng were also used to the plate and mixed with the reagent. The plate was read in a plate reader at 600 nm and samples were calibrated to the standards to determine the concentration of protein. Using the NuPAGE system (Invitrogen), 25 ug of protein was mixed with NuPAGE LDS 4× Sample Buffer (#NP0007), NuPAGE 10× Reducing Agent (#NP0004) and water, mixed well and heated at 96° C. for 15 minutes to denature the protein. The samples were then loaded into 4-12% Bis-Tris gels (Novex (Invitrogen), #0323) with a protein ladder (Novex (Invitrogen) Sharp Pre-stained protein ladder, #57318) and run at 100-120V for about 2 hours with NuPAGE 20×SDS MES Running Buffer (#NP0002) diluted with water. Next, the gel was taken out and loaded into a NuPAGE transfer cassette with a polyvinylidene membrane with NuPAGE 20× Transfer Buffer (#NP0006-1) diluted with water and methanol. Proteins were transferred for 1 hour at 30V at room temperature. Blocking was performed using the Millipore SNAP i.d. Protein Detection system in 0.25% non-fat dry milk in 0.1% Tween in PBS (PBST). Primary antibodies against BMI-1 (Cell Signaling, #6964) and housekeeping control rabbit polyclonal anti-vinculin (1:1000) (Cell Signaling) were incubated overnight with gentle rocking at 4° C. in the blocking solution. The following day, membranes were washed 3 times with PBST in the SNAP i.d. system before being incubated with secondary antibody in blocking buffer for 1 hour at room temperature. Three washes were then performed in the SNAP i.d. system. Protein signals were detected using ECL Western Blotting Substrate (Pierce, #32106) and filmed.

Example 3. Synthesis of N-(4-methoxyphenyl)-4-(2-methylimidaz[1,2-a]pyridin-3-yl)thiazol-2-amine-hydrobromide

Brominated imidazo pyrimidine core (2-bromo-1-(2-methylimidazo[1,2-a]pyridin-3-yl)ethan-1-one) was prepared. To a flask containing 2-bromo-1-(2-methylimidazo [1,2-a]pyridin-3-yl)ethan-1-one 5 (175 mg, 0.691 mmol) in 5 mL MeCN was added 4-methoxyphenylthiourea (126 mg, 0.691 mmol, Oakwood Chemicals) and the reaction was stirred at 60° C. for 18 h and was complete by TLC (5% MeOH/CH$_2$Cl$_2$). The reaction was cooled to ambient temperature and the precipitate that formed was collected by filtration and converted to the free base form to allow for purification via extraction from EtOAc. The organic layer was collected, filtered, and dried to yield Example 3 (135 mg, 58.1%) as the HBr salt as a yellow solid. MS C$_{18}$H$_{16}$N$_4$OS MH+337; $^1$H NMR (400 MHz, DMSO-d$_6$) δ 10.15 (s, 1H), 8.92 (d, J=7.0 Hz, 1H), 7.57-7.48 (m, 3H), 7.24 (t, J=7.8 Hz, 1H), 6.98 (s, 1H), 6.97-6.88 (m, 3H), 3.71 (s, 3H), 2.50 (s, 3H).

Example 4. N-(benzo[d][1,3]dioxol-5-yl)-4-(2-methylimidazo[1,2-a]pyridin-3-yl)thiazol-2-amine hydrobromide

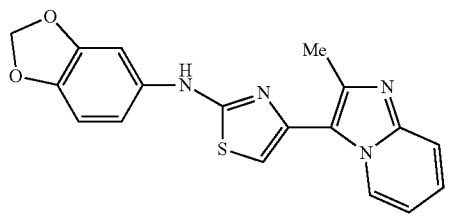 [SMILES: Cc1nc2ccccn2c1-c1csc(Nc2ccc3c(c2)OCO3)n1]

Example 4 was prepared using a procedure similar to that used to prepare Example 3 except that methylenedioxyphenyl thiourea was used. $^1$H NMR (500 MHz, DMSO-d6) δ 10.40 (s, 1H), 9.10 (dt, J=6.9, 1.1 Hz, 1H), 7.98-7.84 (m, 2H), 7.47 (td, J=6.9, 1.4 Hz, 1H), 7.36 (s, 1H), 7.34 (d, J=2.2 Hz, 1H), 6.97 (dd, J=8.4, 2.2 Hz, 1H), 6.87 (d, J=8.4 Hz, 1H), 5.96 (s, 2H), 2.61 (s, 3H).

Example 5. Biological Evaluation

Inhibition of BMI-I Protein Levels

Figure 5:
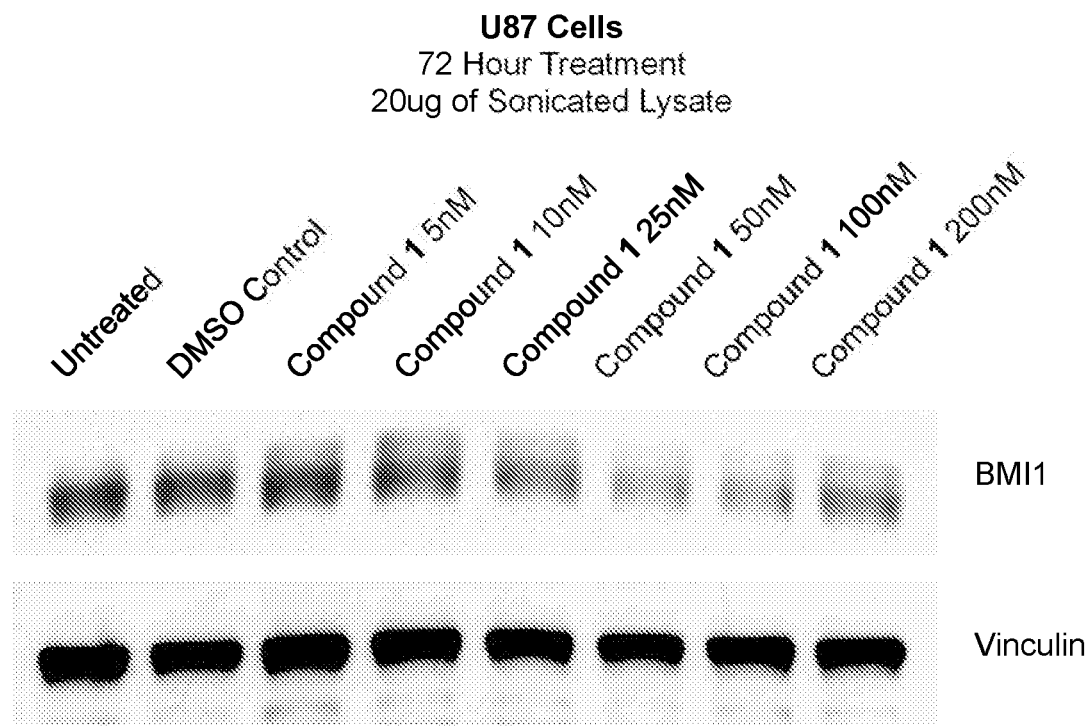
FIG. 5 shows inhibition of BMI-1 protein levels by exemplary compound 1. Western blotting was performed on 20 micrograms of Sonicated U87 glioblastoma cell lysate treated for 72 hours at different concentrations of the inhibitor. Exemplary compound 1 $IC_{50}$ is 10 nM.
Figure 5:
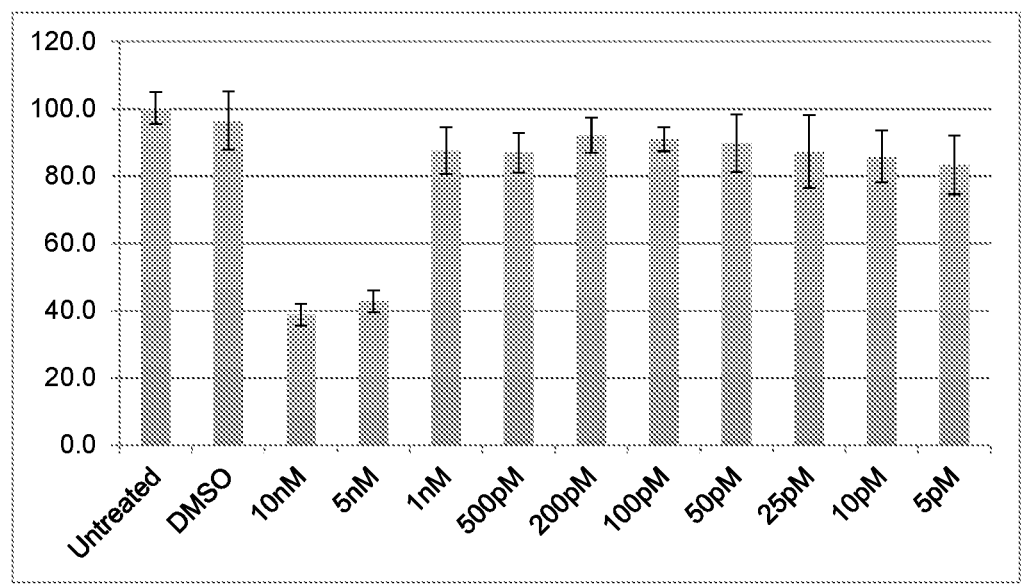

U87 cells were treated with DMSO or different concentrations of the inhibitors for 72 hours. Cells were lysed in Cell Lysis Buffer (Cell Signaling, #9803) supplemented with Protease Inhibitor Cocktail (Sigma, #P8340), sonicated briefly while on ice and spun down for 30 minutes at 4° C., after which the supernatant was collected. For each sample, 2 uL of lysate was mixed well into 198 uL de-ionized water. Next, 10 uL of this diluted sample was added to a well in a 96 well plate in quadruplets and mixed with Protein Assay Dye Reagent Concentrate (Bio-Rad, #500-0006) (which was diluted 1:5 with water). BSA standards of 25 ng, 50 ng, 100 ng, 200 ng and 250 ng were also used to the plate and mixed with the reagent. The plate was read in a plate reader at 600 nm and samples were calibrated to the standards to determine the concentration of protein. Using the NuPAGE system (Invitrogen), 25 ug of protein was mixed with NuPAGE LDS 4× Sample Buffer (#NP0007), NuPAGE 10× Reducing Agent (#NP0004) and water, mixed well and heated at 96° C. for 15 minutes to denature the protein. The samples were then loaded into 4-12% Bis-Tris gels (Novex (Invitrogen), #0323) with a protein ladder (Novex (Invitrogen) Sharp Pre-stained protein ladder, #57318) and run at 100-120V for about 2 hours with NuPAGE 20×SDS MES Running Buffer (#NP0002) diluted with water. Next, the gel was taken out and loaded into a NuPAGE transfer cassette with a polyvinylidene membrane with NuPAGE 20× Transfer Buffer (#NP0006-1) diluted with water and methanol. Proteins were transferred for 1 hour at 30V at room temperature. Blocking was performed using the Millipore SNAP i.d. Protein Detection system in 0.25% non-fat dry milk in 0.1% Tween in PBS (PBST). Primary antibodies against BMI-1 (Cell Signaling, #6964), mouse monoclonal anti-ubiquityl (γ)-histone H2A clone E6C5 (1:1,000) (Millipore) and housekeeping control rabbit polyclonal anti-vinculin (1:1000) (Cell Signaling) were incubated overnight with gentle rocking at 4° C. in the blocking solution. The following day, membranes were washed 3 times with PBST in the SNAP i.d. system before being incubated with secondary antibody in blocking buffer for 1 hour at room temperature. Three washes were then performed in the SNAP i.d. system. Protein signals were detected using ECL Western Blotting Substrate (Pierce, #32106) and filmed. Results are shown in FIG. 5.

Cell Viability in Primary Patient-Derived Glioblastoma (GBM) Cells

Figure 6:
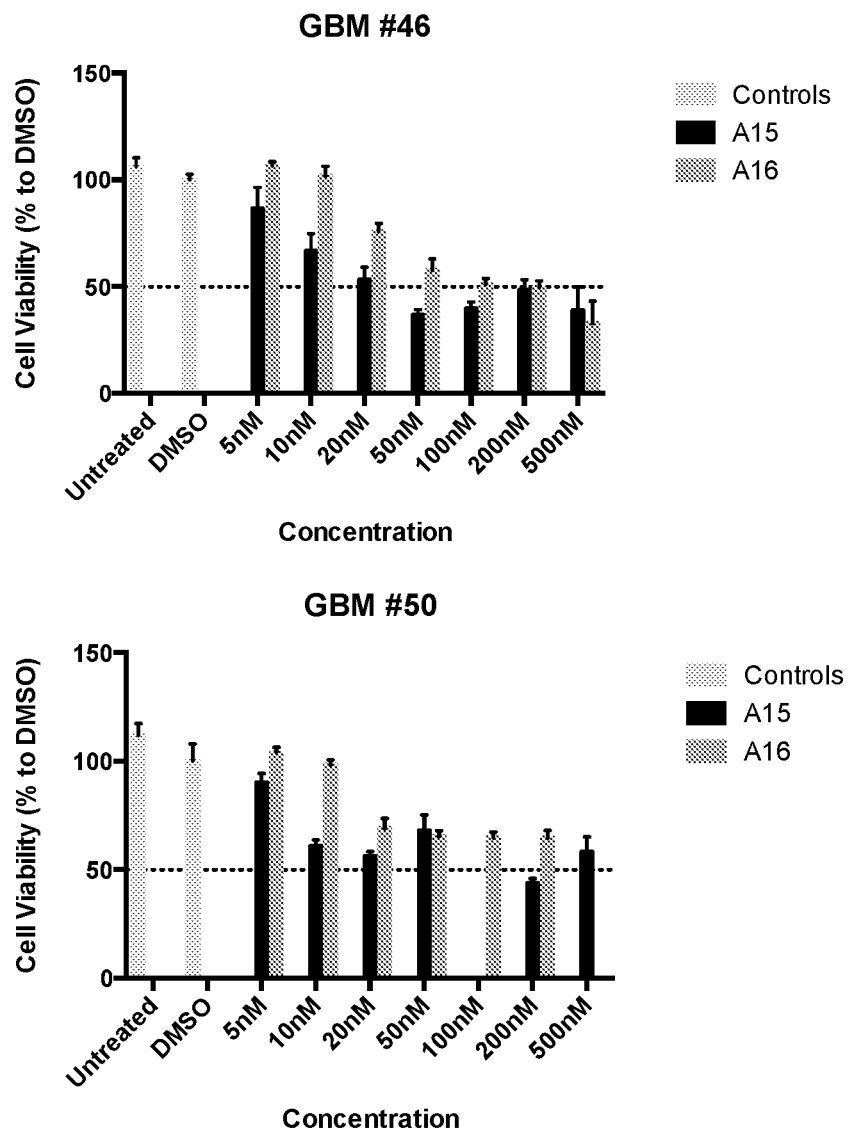
FIG. 6 shows cell Viability in primary patient-derived glioblastoma (GBM) cells (GBM #46, GBM #50, and GBM #76). Example 3 is labeled as A15 and exemplary compound 2 is labeled as A16.
Figure 6:
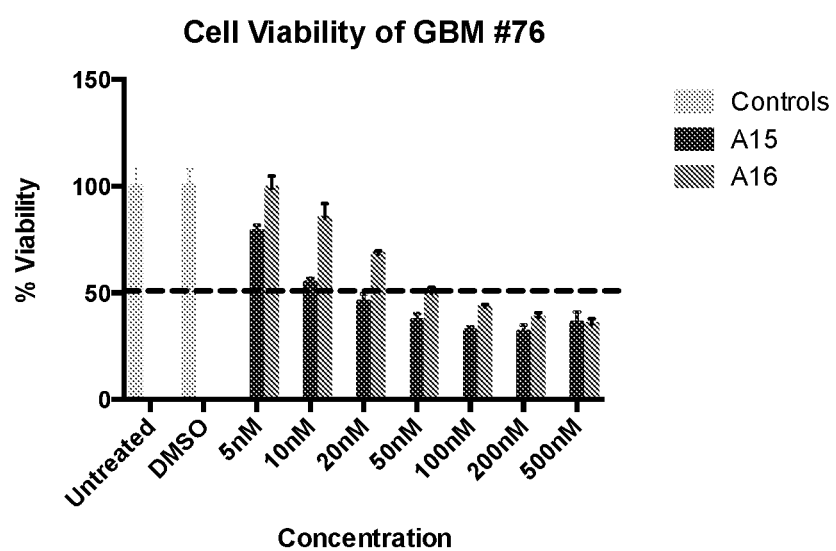

To generate primary patient-derived GBM models for testing small molecule inhibitors, fresh primary tissues were received from patients undergoing surgical resection of WHO grade IV gliomas at Robert Wood Johnson University Hospital (RWJUH) under an approved IRB protocol. De-identified primary human GBM samples were delivered to the laboratory. Cells were obtained through mechanical dissociation of the tumor tissue using a blade and plated in DMEM/F12 medium (Gibco) in the presence of B-27 Supplement (Gibco, #17504-044), 20 ng/ml of human recombinant EGF (Gibco, #PHG0311L) and human recombinant FGF (Peprotech, #AF-100-18B). The following day, the culture was collected, incubated with Accutase (Gibco, #A11105-01) at 37° C. and passed through a 26G×⅜ needle (BD Precision Glide, #305110) to obtain a single cell suspension and re-plated in the same supplemented medium. Cells were cultured at low (5-6) passages in serum-free sphere 3D culture with mitogens that preserve the clonogenic stemness phenotype. Four different primary GBM cells (GBM #46, GBM #50, and GBM #76) were tested for cell viability after treatment with the inhibitors. Cell viability was measured using MTT assay. Briefly, one thousand cells per well were seeded in 96-well plates and exposed to drug in a total of 200 uL media. After 72 hours, 50 uL of stock concentration of 2.5 mg/mL 3-(4,5-dimethylthiazol-2-yl)-2,5-diphenyltetrazolium bromide (MTT) (Sigma, #M2128) dissolved in PBS was added to wells and incubated at 37° C. for 4 hours; read in a fluorescent plate reader at 570 nm and compared to DMSO and untreated cells. The $IC_{50}$ (defined as the concentration at which 50% of the cells were viable) was determined from the curve. Results are shown in FIG. 6.

Comparison of Example 3 and PTC-209 in the Same Cell Type (U87 Glioblastoma Cells)

BMI-1 inhibitors were developed by the Molecular Design and Synthesis laboratory, Rutgers Translational Sciences at Rutgers University, NJ, USA. C209 (Generic name is PTC-209) was characterized among a screen for post-transcriptional inhibitors of BMI-1. Zebrafish embryo toxicology assays were used to select RU-A compounds with no embryonic toxicity in vivo (a surrogate assay for toxic effects on normal stem cells). The $IC_{50}$ values in U87 and GBM sphere cells were determined using MTT assays (as described above), and exemplary Example 3 was the most potent, but had no significant effects on normal astrocytes and embryo assays. To compare the effects of Example 3 to PTC-209, U87 cells ($3\times10^5$/well) were seeded into the 96-well tissue culture plates, and treated with different BMI-1 inhibitors (from 10 nM to 10 µM) in appropriate media. Dose response curves were generated upon exposing U87 cells to different concentrations of exemplary compounds and PTC-209 (0.010-10 µM) for 72 hours. Cells were counted using Beckman Coulter Vi-CELL Cell Viability Analyzer, and cell viability was confirmed by CellTiter-Glo Luminescent Cell Viability Assay (Promega, Madison, Wis., USA) according to standard protocols and analyzed with a Victor 2 plate reader (Wallac, Turku, Finland).

Figure 7:
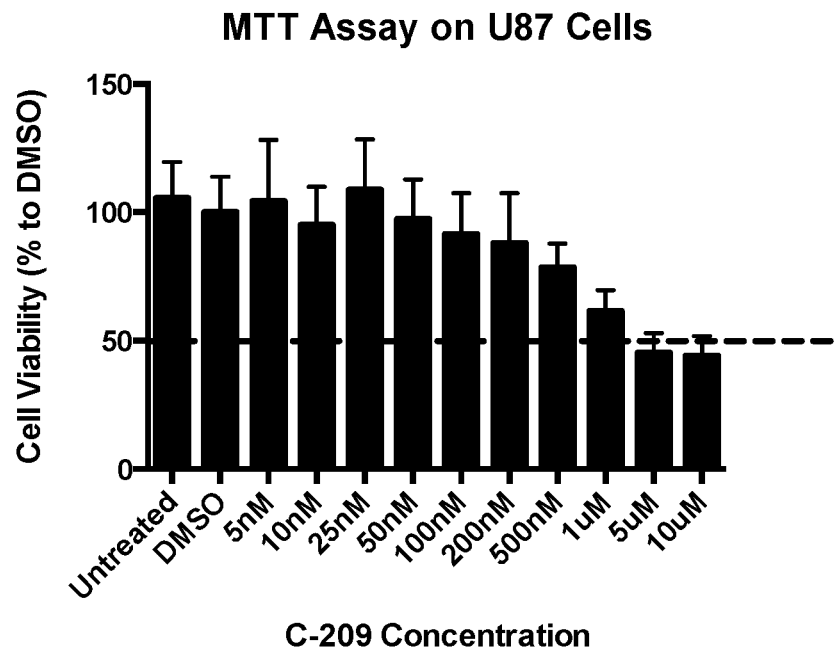
FIG. 7 shows comparison of Example 3 and PTC-209 in the same cell type (U87 glioblastoma cells). Example 3 $IC_{50}$ is 10 nM in U87 cells, while PTC-209 $IC_{50}$ is 10 μM. Thus, Example 3 is one thousand-fold more potent than PTC-209.
Figure 8:
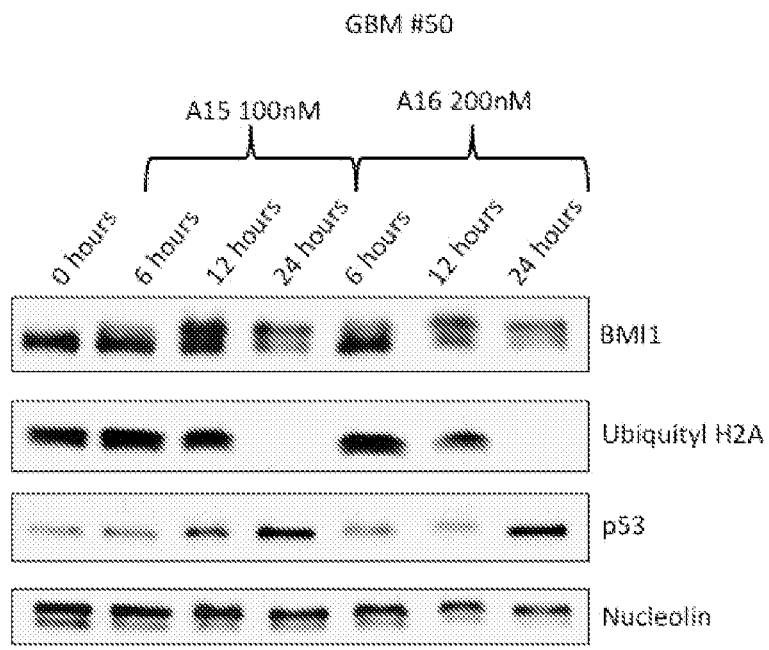
FIG. 8 shows dynamics of inhibition of BMI-1 protein levels showed by Western blotting. Examples 3 and 4 inhibit BMI-1, inhibit ubiquitin H2A and increase WT p53 levels in primary glioblastoma cells. Example 3 is labeled as A15 and Example 4 is labeled as A16.

The selectivity and potency in U87 cells were assessed vs primary GBM. Dose-response curves were generated in both spheres and monocultures and used to determine a sphere selectivity ratio (targeting Glioblastoma Initiating Cells), defined as $EC_{50}$(U87)/$EC_{50}$(spheres), for each compound. Compounds that had a sphere selectivity ratio greater than controls (DMSO and Temozolomide) could be defined as agents with high selectivity for glioblastoma cancer stem cells (Example 3). Results are shown in FIG. 7

Dynamics of Inhibition of BMI-I Protein Levels

To study the compound dynamic activity against GBM spheres, GBMs were tested with exemplary compounds. Different GBM cells were treated with DMSO or different concentrations of the inhibitors for 72 hours. Cells were lysed in Cell Lysis Buffer (Cell Signaling, #9803) supplemented with Protease Inhibitor Cocktail (Sigma, #P8340), spun down for 30 minutes at 4° C., after which the supernatant was collected at every time point indicated. Western blotting analysis was performed on all samples as described above. GBM#50 showed a dose-dependent loss of BMI-1 protein expression at 72 h when treated with as low as 25 nM of RU-A15. BMI-1 loss started at 6-12 h, coinciding with an upper shift and hyper-phosphorylation of BMI-1 at 12-24 h and complete depletion at 72 h. The treatment with these inhibitors caused a dose-dependent reduction in BMI-1 and this was also associated with reduction in lysine-119 mono-ubiquitin form of gH2A, a specific product of BMI-1 (PRC1) activity. RU-A15/A16 treatment induced upregulation of the CDK inhibitor p21 in GBM#46 and #50. This is expected since BMI-1 is known to suppress p21. BMI-1 inhibition could be reversed using phosphatase treatment, moreover, when proteasomal inhibitor is added to treated cells after 24 h, BMI-1 is locked in the phosphorylated state, therefore showing that the phosphorylation event precedes BMI-1 degradation. The phosphorylation was independent of p38 kinase activation, as when we added SB2020190, the p38 inhibitor to the cultured cells upon treatment with the BMI-1 inhibitor, the combined treatment could not reverse the effects of RU-A15 on BMI-1 inhibition.

Removal of the Binding Pocket Abrogate the Effects of Exemplary Compounds

BMI-1 RNA has a unique 5'UTR three-dimensional (3D) structure using in silico assays, suggesting that cap-dependent translation could be repressed, and an internal ribosomal entry site (IRES) may allow alternative translation initiation. Since translation initiation is dependent on RNA folding, the 3D folding of the BMI-1 5'UTR was examined. To identify sequences that fold into a target minimum and maximum free energy (MFE) secondary structure, inverse RNA folding of the BMI-1 5'UTR was performed using the mFold server. A highly probable, probability annotated group of secondary structures were identified, starting with the MFE, centroid energy structures and including fourteen other probabilities. In silico docking studies (UCSF DOCK program) done with 3D structural models of BMI-1 was used, built by homology modeling using Modeler 9v8, to reveal that RU-A15 could bind to a pocket formed in the BMI-1 5'UTR RNA minor groove fold structures. In a luciferase plasmid containing the BMI-1 5'UTR, the sequences of the pocket region that contains the potential binding site was removed by cutting with compatible restriction enzymes and re-ligating the plasmid. The luciferase activity was examined with the luc plasmids or without the binding pocket upon treatment with the inhibitors. RU-A15 or A16 treatment significantly reduced normalized luc in cells harboring the BMI-1 5'UTR with an intact minor groove potential binding pocket but not when the pocket sequences were removed. Thus, RU-A15/A16 engages with the BMI-1 UTR regulatory mechanisms.

Figure 9:
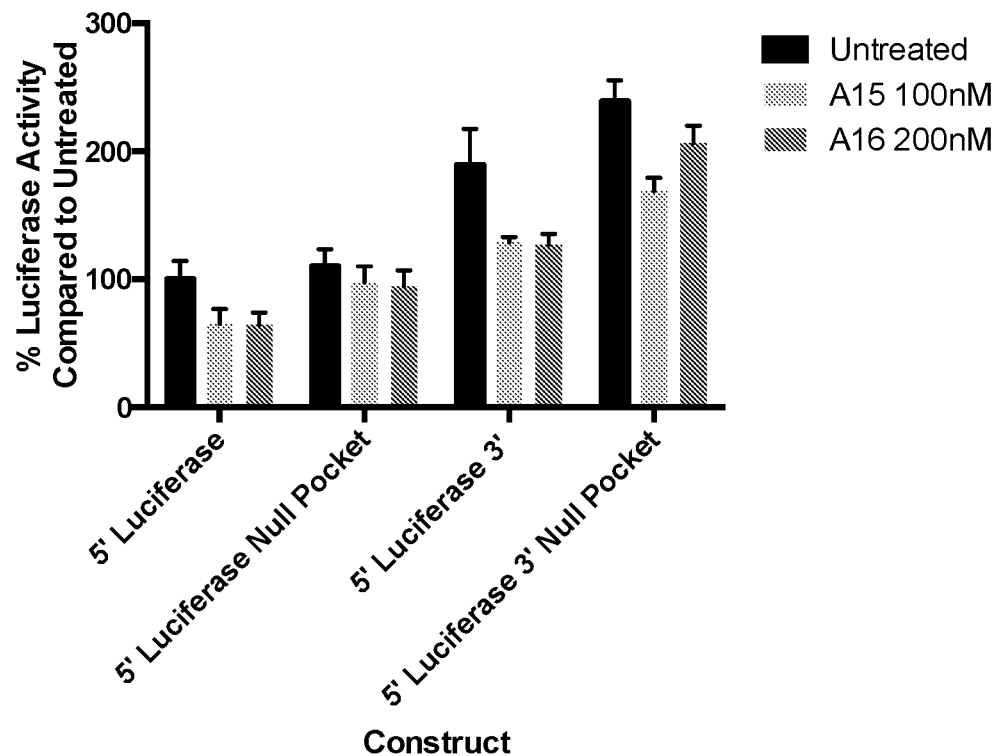
FIG. 9 shows that Examples 3 and 4 work by novel mechanism through binding to the untranslated RNA. Removal of the binding pocket abrogate the effects of Examples 3 and 4. Example 3 is labeled as A15 and Example 4 is labeled as A16.

Next, to test if Examples 3 and 4 are selective for BMI-1 RNA, cells were concomitantly treated with RU-A15/16 (100 nM, 200 nM, respectively) and cyclohexamide (CHX), a general translational inhibitor, and analyzed mRNA expression of BMI-1 and the CHX-specific target epithelial sodium channel (αENaC). While CHX mutually lowered mRNA levels of both BMI-1 and αENaC, RU-A15/16 did not inhibit BMI-1 or αENaC mRNA. Results are shown in FIG. 9.

Examples 6-12

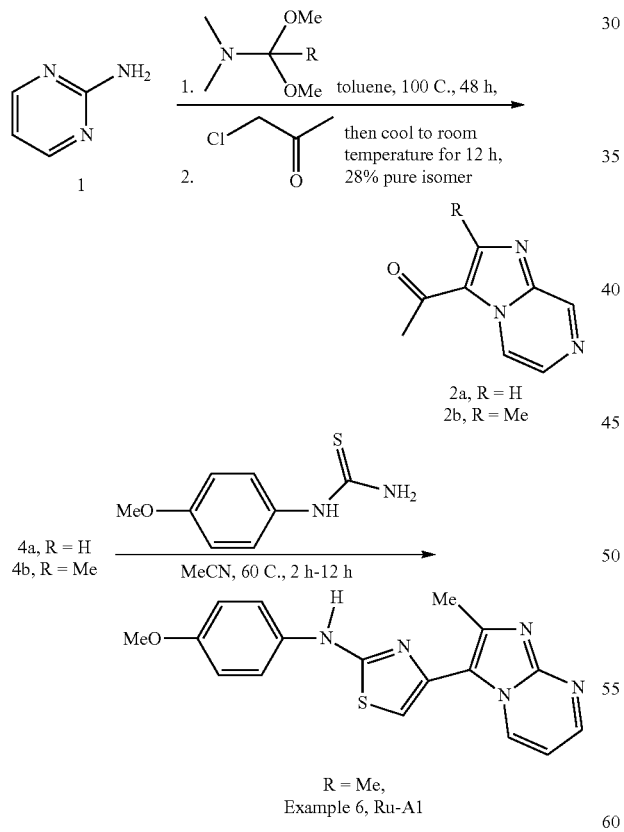

R = Me,
Example 6, Ru-A1

Chemistry

The chemistry to prepare Examples 6-12 is illustrated in Scheme 1. To prepare the imidazopyrimidine core, 2-aminopyrimidine 1 was treated first with N,N-dimethylformamide dimethyl acetal followed by 2-chloroacetone in toluene at 100 C for 48 h to give 1-(imidazo[1,2-a]pyrimidin-3-yl) ethan-1-one 2a. Alternatively, 2-aminopyrimidine 1 was treated first with N,N-dimethylacetamide dimethyl acetal followed by 2-chloroacetone in toluene at 100° C. for 48 hours to give 1-(2-methylimidazo[1,2-a]pyrimidin-3-yl) ethan-1-one 2b. Each condensation produced a mixture of regioisomers at the 1 and 2 positions of the imidazopyrimidine and chromatographic purification afforded 2a and 2b. Subsequent bromination gave the brominated ketones 4a and 4b that were subsequently condensed with the requisite substituted arylthioureas to afford the final thiazoles as crystalline solid hydrobromide salts. The preparation of the compound of Example 6 (also RU-A1) is illustrated in Scheme 1.

Example 6. N-(4-methoxyphenyl)-4-(2-methylimidazo[1,2-a]pyrimidin-3-yl)thiazol-2-amine hydrobromide (Example 6, also RU-A1)

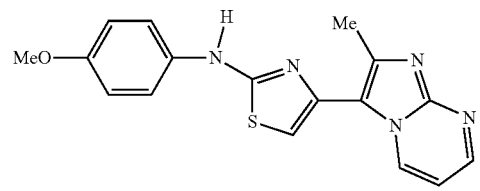 [SMILES: COc1ccc(Nc2nc(-c3c(C)nc4ncccn34)cs2)cc1]

To a flask containing 2-bromo-1-(2-methylimidazo[1,2-a]pyrimidin-3-yl)ethan-1-one 4b (101 mg, 0.40 mmol) in 4 mL MeCN was added 4-methoxyphenylthiourea (73 mg, 0.40 mmol, Oakwood Chemicals) and the reaction was stirred at 60° C. for 2 h and was complete by TLC (5% MeOH/EtOAc). The reaction was cooled to ambient temperature and the precipitate that formed was collected by filtration to give 130 mg of a pale yellow solid. Recrystallization from minimal MeOH to which EtOAc was added gave 58 mg (43%) of the title compound as the HBr salt as a yellow crystalline solid. MS $C_{17}H_{15}N_5OS$, MH+338; $^1$H NMR (400 MHz, DMSO-$d_6$) δ 10.33 (s, 1H), 9.56 (d, J=6.7 Hz, 1H), 8.95 (s, 1H), 7.70-7.59 (m, 1H), 7.53 (d, J=8.4 Hz, 2H), 7.36 (s, 1H), 6.94 (d, J=8.6 Hz, 2H), 3.73 (s, 3H), 2.67 (s, 3H).

Example 7. N-(benzo[d][1,3]dioxol-5-yl)-4-(2-methylimidazo[1,2-a]pyrimidin-3-yl)thiazol-2-amine hydrobromide

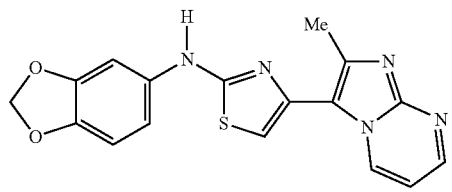 [SMILES: Cc1nc2ncccn2c1-c1csc(Nc2ccc3c(c2)OCO3)n1]

To a flask containing 2-bromo-1-(2-methylimidazo[1,2-a]pyrimidin-3-yl)ethan-1-one 4b 200 mg, 0.79 mmol) in 5 mL MeCN was added 1-(3,4-methylenedioxyphenyl-2-thiourea (196 mg, 0.79 mmol) and the reaction was stirred at 60° C. for 2 h and then cooled to ambient temperature, stirred overnight, and was complete by TLC (5% MeOH/EtOAc). The precipitate that formed was collected by filtration to give 194 mg of a pale yellow solid that was washed with MeCN and air dried to give 190 mg (70%) of the title compound as the HBr salt as a light yellow solid. MS $C_{17}H_{13}N_5O_2S$ MH+, 352; $^1$H NMR (400 MHz, DMSO-$d_6$) δ 10.44 (s, 1H), 9.56 (d, J=6.9 Hz, 1H), 9.02 (d, J=3.5 Hz, 1H), 7.74-7.67 (m, 1H), 7.43 (s, 1H), 7.34 (s, 1H), 6.99 (d, J=8.3 Hz, 1H), 6.90 (d, J=8.2 Hz, 1H), 5.99 (s, 2H), 2.67 (s, 3H).

Example 8. N-(2,4-dimethoxyphenyl)-4-(2-methylimidazo[1,2-a]pyrimidin-3-yl)thiazol-2-amine hydrobromide (Example 8, also RU-A5)

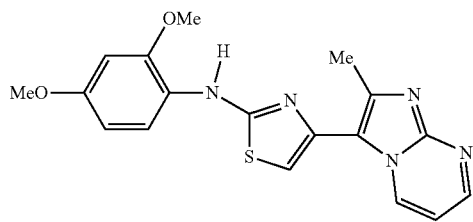 [SMILES: COc1ccc(Nc2nc(-c3c(C)nc4ncccn34)cs2)c(OC)c1]

To a flask containing 2-bromo-1-(2-methylimidazo[1,2-a]pyrimidin-3-yl)ethan-1-one 4b (101 mg, 0.40 mmol) in 5 mL MeCN was added 2,4-dimethoxyphenylthiourea (167 mg, 0.790 mmol) and the reaction was stirred at 60° C. for 2 h and was complete by TLC (5% MeOH/EtOAc). The reaction was cooled to ambient temperature and the precipitate that formed was collected by filtration to give 185 mg of a light orange solid. Recrystallization from minimal MeOH to which EtOAc was added led to the formation of 87 mg (30%) of the title compound as the HBr salt as a white crystalline solid. MS $C_{18}H_{17}N_5O_2S$, MH+368, $^1$H NMR (400 MHz, DMSO-$d_6$) δ 9.69-9.61 (m, 2H), 9.06-8.99 (m, 1H), 7.81 (d, J=8.7 Hz, 1H), 7.75-7.68 (m, 1H), 7.33 (s, 1H), 6.69 (s, 1H), 6.53 (d, J=8.5 Hz, 1H), 3.85 (s, 3H), 3.77 (s, 3H), 2.67 (s, 3H).

Example 9. 4-(imidazo[1,2-a]pyrimidin-3-yl)-N-(4-methoxyphenyl)thiazol-2-amine hydrobromide

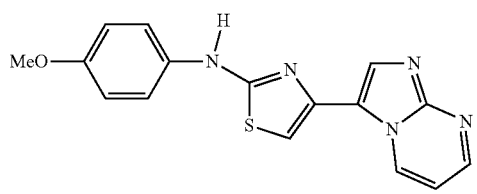 [SMILES: COc1ccc(Nc2nc(-c3cnc4ncccn34)cs2)cc1]

To a flask containing 2-bromo-1-(imidazo[1,2-a]pyrimidin-3-yl)ethan-1-one 4a (500 mg, 2.09 mmol) in 10 mL MeCN was added 4-methoxyphenylthiourea (381 mg, 2.09 mmol) and the reaction was stirred at 60° C. for 6 h and was complete by TLC (5% MeOH/EtOAc). The reaction was cooled to ambient temperature and the precipitate that formed was collected by filtration and washed with MeCN to give 590 mg of an orange solid. Recrystallization from minimal MeOH to which EtOAc was added led to the overnight formation of 111 mg (17% first crop, analytically pure) of the title compound as the HBr salt as a yellow crystalline solid. MS $C_{16}H_{13}N_5OS$, MH+324; $^1$H NMR (400 MHz, DMSO-$d_6$) δ 10.32 (s, 1H), 9.74 (d, J=7.0 Hz, 1H), 8.98 (s, 1H), 8.65 (s, 1H), 7.71-7.64 (m, 1H), 7.54 (d, J=7.9 Hz, 2H), 7.48 (s, 1H), 6.97 (d, J=8.9 Hz, 2H), 3.75 (s, 3H).

Example 10. N-(4-methoxyphenyl)-5-methyl-4-(2-methylimidazo[1,2-a]pyrimidin-3-yl)thiazol-2-amine hydrobromide

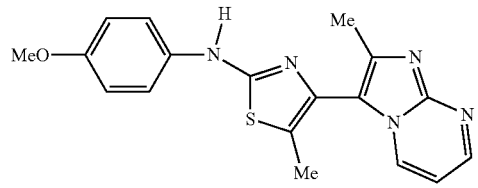 [SMILES: COc1ccc(Nc2nc(-c3c(C)nc4ncccn34)c(C)s2)cc1]

Brominated imidazo pyrimidine core (2-bromo-1-(imidazo[1,2-a]pyrimidin-3-yl)propan-1-one) 3 was prepared as follows. To a flask containing 2-bromo-1-(imidazo[1,2-a]pyrimidin-3-yl)propan-1-one 3 (200 mg, 0.75 mmol) in 5 mL MeCN was added 4-methoxyphenylthiourea (137 mg, 0.75 mmol) and the reaction was stirred at 68° C. for 3.5 h and was complete by TLC (5% MeOH/EtOAc). The reaction was evaporated and purified by reverse phase column (25% MeOH—$H_2O$) and gave 85 mg (25%) of the title compound as the HBr salt as a light yellow solid. MS $C_{18}H_{17}N_5OS$, MH+352; $^1$H NMR (400 MHz, DMSO-$d_6$) δ 10.00 (s, 1H), 8.64 (d, J=6.4 Hz, 1H), 8.53 (s, 1H), 7.48 (d, J=8.1 Hz, 2H), 7.10-7.01 (m, 1H), 6.86 (d, J=7.8 Hz, 2H), 3.69 (s, 3H), 2.36 (s, 3H), 2.21 (s, 3H).

Example 11. N-(4-methoxy-2-methylphenyl)-4-(2-methylimidazo[1,2-a]pyrimidin-3-yl)thiazol-2-aminehydrobromide

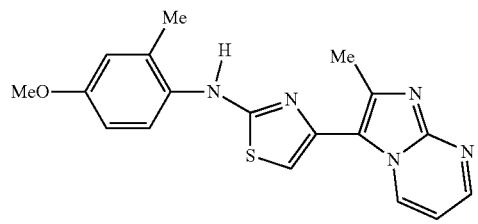 [SMILES: COc1ccc(Nc2nc(-c3c(C)nc4ncccn34)cs2)c(C)c1]

To a flask containing 2-bromo-1-(2-methylimidazo[1,2-a]pyrimidin-3-yl)ethan-1-one 4b (117 mg, 0.46 mmol) in 5 mL MeCN was added 2-methoxy-2-methylphenylthiourea (90 mg, 0.46 mmol) and the reaction was stirred at 60° C. for 2 h and was complete by TLC (5% MeOH/EtOAc). The reaction was evaporated and purified by reverse phase column (25% MeOH—$H_2O$) and gave 45 mg (13%) of the title compound as the HBr salt as a light yellow solid in two consecutive fractions. MS $C_{18}H_{17}N_5OS$ MH+352; $^1$H NMR (400 MHz, DMSO-$d_6$) δ 9.47-9.37 (m, 2H), 8.55 (s, 1H), 7.52 (d, J=9.0 Hz, 1H), 7.20-7.10 (m, 1H), 6.99 (s, 1H), 6.88 (s, 1H), 6.82 (d, J=9.0 Hz, 1H), 3.75 (s, 3H), 2.56 (s, 3H), 2.26 (s, 3H).

Example 12. N-(2-methoxyphenyl)-4-(2-methylimidazo[1,2-a]pyrimidin-3-yl)thiazol-2-amine hydrobromide (Example 12, also RU-A12)

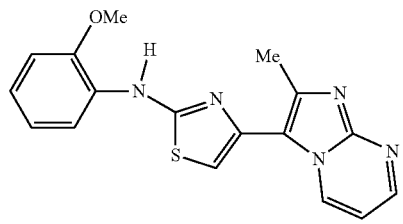 [SMILES: COc1ccccc1Nc1nc(-c2c(C)nc3ncccn23)cs1]

To a flask containing 2-bromo-1-(2-methylimidazo[1,2-a]pyrimidin-3-yl)ethan-1-one 4b (100 mg, 0.394 mmol) in 5 mL MeCN was added 1-(2-methoxyphenyl)thiourea (71.8 mg, 0.394 mmol, Aldrich Chemistry) and the reaction was stirred at 60° C. for 6 h and was complete by TLC (5% MeOH/CH$_2$Cl$_2$). The reaction was cooled to ambient temperature and then was cooled further in the refrigerator. The precipitate that formed was collected by filtration and washed with MeCN (2×10 mL). The final product was collected to afford 67 mg (50%) of the title compound as the HBr salt as a yellow crystalline solid. MS C$_{17}$H$_{15}$N$_5$OS MH$^+$338; $^1$H NMR (400 MHz, DMSO-d$_6$) δ 9.91 (s, 1H), 9.60 (d, J=6.8 Hz, 1H), 9.05-8.98 (m, 1H), 8.17 (d, J=7.9 Hz, 1H), 7.74-7.67 (m, 1H), 7.44 (s, 1H), 7.12-7.00 (m, 2H), 6.94 (t, J=7.2 Hz, 1H), 3.89 (s, 3H), 2.68 (s, 3H).

Additional biological data for representative compounds of the invention can be found at Bartucci, M., et al., *Targ Oncol*, 2017, 12, 449-462 and in the Supplemental Materials associated therewith.

Example 13

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents (including Bartucci, M., et al., *Targ Oncol*, 2017, 12, 449-462 and the Supplemental Materials associated therewith) are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A method for treating radiation and/or temozolomide resistant glioblastoma in a human comprising administering to the human an effective amount of a compound of formula (Ic):

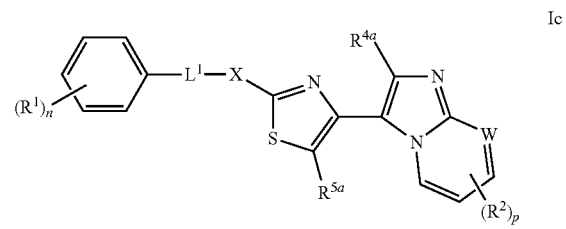

or a pharmaceutically acceptable salt thereof, wherein:
W is CH or N;
each R$^1$ is independently selected from the group consisting of hydroxy, halo, cyano, nitro, C$_{1-6}$ alkyl, C$_{1-6}$ alkoxy, C$_{1-6}$ alkanoyl, C$_{1-6}$ alkoxycarbonyl, C$_{2-6}$ alkanoyloxy, and —N(R$^a$)$_2$, wherein any C$_{1-6}$ alkyl or C$_{1-6}$ alkoxy is optionally substituted with one or more halo; or any two adjacent R$^1$ groups taken together form methylenedioxy or ethylenedioxy;

each $R^2$ is independently selected from the group consisting of hydroxy, halo, cyano, nitro, $C_{1-6}$ alkyl, $C_{1-6}$ alkoxy, $C_{1-6}$ alkanoyl, $C_{1-6}$ alkoxycarbonyl, $C_{2-6}$ alkanoyloxy, and —$N(R^a)_2$, wherein any $C_{1-6}$ alkyl or $C_{1-6}$ alkoxy is optionally substituted with one or more halo; or any two adjacent $R^2$ groups taken together form methylenedioxy or ethylenedioxy;

$L^1$ is absent or $C_{1-4}$ alkylene;

X is —$NR^x$—;

$R^{4a}$ is selected from the group consisting of hydrogen and $C_{1-6}$ alkyl that is optionally substituted with one or more halo;

$R^{5a}$ is selected from the group consisting of hydrogen and $C_{1-6}$ alkyl that is optionally substituted with one or more halo;

each $R^a$ is independently hydrogen or $C_{1-4}$ alkyl; or two $R^a$ groups taken together with the nitrogen to which they are attached form pyrrolidinyl, piperidinyl, piperazinyl or morpholinyl;

$R^x$ is hydrogen or $C_{1-4}$ alkyl;

n is 0, 1, 2, 3 or 4; and p is 0, 1, 2 or 3.

2. The method of claim 1, wherein the compound of formula Ic is a compound of formula:

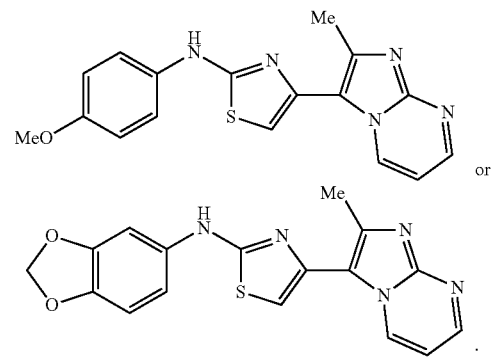

or

3. The method of claim 1, wherein the compound of formula Ic is a compound of formula:

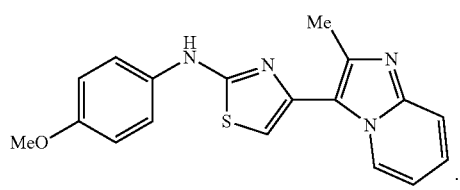 [SMILES: COc1ccc(Nc2nc(-c3c(C)nc4ccccn34)cs2)cc1]

* * * * *

UNITED STATES PATENT AND TRADEMARK OFFICE
CERTIFICATE OF CORRECTION

PATENT NO. : 10,875,861 B1
APPLICATION NO. : 16/553053
DATED : December 29, 2020
INVENTOR(S) : David J. Augeri and Hatem E. Sabaawy Page 1 of 1

It is certified that error appears in the above-identified patent and that said Letters Patent is hereby corrected as shown below:

In the Claims

Column 32, Lines 1-14, Claim 2, please delete " 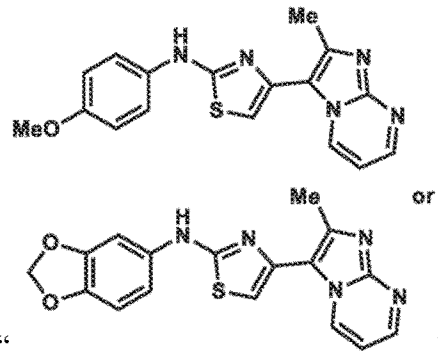 " and insert

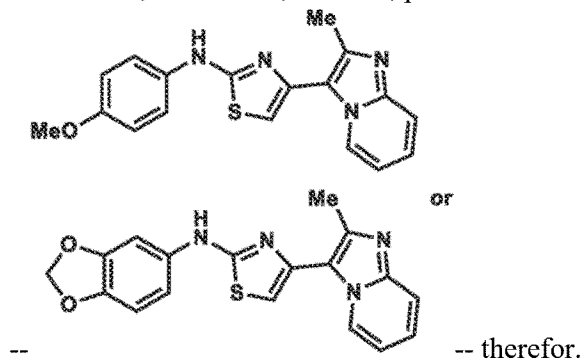

-- therefor.

Signed and Sealed this
Second Day of March, 2021

Drew Hirshfeld
*Performing the Functions and Duties of the
Under Secretary of Commerce for Intellectual Property and
Director of the United States Patent and Trademark Office*